(12) United States Patent
Nitta

(10) Patent No.: US 9,182,349 B2
(45) Date of Patent: Nov. 10, 2015

(54) CELL NUCLEUS OBSERVATION SUBSTRATE AND CELL NUCLEUS OBSERVATION APPARATUS

(75) Inventor: Nao Nitta, Tokyo (JP)

(73) Assignee: SONY CORPORATION, Tokyo (JP)

(*) Notice: Subject to any disclaimer, the term of this patent is extended or adjusted under 35 U.S.C. 154(b) by 11 days.

(21) Appl. No.: 13/977,417

(22) PCT Filed: Dec. 27, 2011

(86) PCT No.: PCT/JP2011/007293
§ 371 (c)(1),
(2), (4) Date: Jun. 28, 2013

(87) PCT Pub. No.: WO2012/095935
PCT Pub. Date: Jul. 19, 2012

(65) Prior Publication Data
US 2013/0288351 A1 Oct. 31, 2013

(30) Foreign Application Priority Data

Jan. 13, 2011 (JP) ................................. 2011-005240

(51) Int. Cl.
*C12M 1/00* (2006.01)
*C12M 3/00* (2006.01)
(Continued)

(52) U.S. Cl.
CPC .............. *G01N 21/6486* (2013.01); *G01N 1/30* (2013.01); *G01N 21/6428* (2013.01); *G01N 21/6458* (2013.01)

(58) Field of Classification Search
CPC . G01N 1/30; G01N 21/6428; G01N 21/6458; G01N 21/6486
USPC ............................................ 435/283.1–309.4
See application file for complete search history.

(56) References Cited

U.S. PATENT DOCUMENTS

2011/0136154 A1* 6/2011 Geddes ......................... 435/7.92
2012/0122139 A1* 5/2012 Park et al. ...................... 435/29

FOREIGN PATENT DOCUMENTS

JP 2003-107081 4/2003

OTHER PUBLICATIONS

Zimmerman et al., "Diagnosis of Malaria by Magnetic Deposition Microscopy," Am. J. Trop. Med. Hyg., 74(4), 2006, pp. 568-572. (5 pages).

(Continued)

*Primary Examiner* — Nathan Bowers
*Assistant Examiner* — Lydia Edwards
(74) *Attorney, Agent, or Firm* — Hazuki International, LLC

(57) ABSTRACT

To provide a technology of staining nuclei of cells, microorganisms and the like by a simple operation and observing their forms.
There is provided a cell nucleus observation substrate including an introduction part into which a sample liquid containing cells is introduced and an observation area within which the cells in the sample liquid introduced from the introduction part is held, copper being disposed on a flow path of the sample liquid in the introduction part and the observation area so that the copper being capable of contacting with the sample liquid. In the cell nucleus observation substrate, the cells in the sample liquid introduced from the introduction part is contacted with copper, nucleic acids therein will emit fluorescence and is held within the observation area. Accordingly, in the cell nucleus observation substrate, the cells including the nuclei being fluorescence stained can be observed at the observation area.

7 Claims, 33 Drawing Sheets

(51) Int. Cl.
C12M 1/34 (2006.01)
G01N 21/64 (2006.01)
G01N 1/30 (2006.01)

(56) References Cited

OTHER PUBLICATIONS

Karl et al., "Enhanced detection of gametocytes by magnetic deposition microscopy predicts higher potential for Plasmodium falciparum transmission," Malaria Journal 2008, 7:66, Apr. 25, 2008. (9 pages).
Apoulson, D.F., "Abstracts of Papers Presented at the 1950 Meetings of the Genetics Society of America," Columbus, Ohio, Sep. 11-14, 1950. (3 pages).
V. T. Bowen et al., "The Chemistry and Physiology of the Nucleus," Proceedings of the Symposium held Aug. 1951 by the Biology Department, Brookhaven National Laboratory. (11 pages).
B. K. Filshie et al., "Ultrastructure of the Copper-Accumulating Region of the Drosophila Larval Midgut," Tissue & Cell 1971 3 (1) pp. 77-I02. (26 pages).
Bienz et al., "Specification of a Single Cell Type by a Drosophila Homeotic Gene," Cell, vol. 76, pp. 689-702, Feb. 25, 1994. (14 pages).
Bienz et al.. "Two different thresholds of wingless signalling with distinct developmental consequences in the Drosophila midgut," The EMBO Journal, vol. 14, No. 20, pp. 5016-5026, 1995. (11 pages).
Atkinson et al., "Calcium-Activated Potassium Channel Gene Expression in the Midgut of Drosophila," Comp. Biochem. Physiol. vol. 118B, No. 2, pp. 411-420, 1997. (10 pages).
McNulty et al., "Evidence that a copper-metallothionein complex is responsible for fluorescence in acid-secreting cells of the Drosophila stomach," Cell Tissue Res (2001) 304:383-389. (7 pages).
Jan A. Veenstra, "Peptidergic paracrine and endocrine cells in the midgut of the fruit fly maggot," Cell Tissue Res (2009) 336:309-323. (15 pages).
Stillman, et al., "A luminescence probe for metallothionein in liver tissue: emission intensity measured directly from copper metallothionein induced in rat liver," Nov. 1989, vol. 257, No. 2, pp. 283-286. (4 pages).
Okabe et al., "Direct Visualization of Copper-Metallothionein in LEC Rat Kidneys: Application of Autofluorescence Signal of Copper-Thiolate Cluster," The Journal of Histochemistry and Cytochemistry, vol. 44, No. 8, pp. 865-873, 1996. (9 pages).
Presta et al., "Incorporation of Copper into the Yeast Saccharomyces cerevisiae. Identification of Cu(I)-Metallothionein in Intact Yeast Cells," Journal of Inorganic Biochemistry.
Quaglia et al., "Copper-Metallothionein Autofluorescence," Hepatology, vol. 50, No. 4, 2009, pp. 1312-1313. (2 pages).
M. Beltramini et al., "Luminescence Properties of Neurospora Copper Metallothionein," FEBS Letters, vol. 127, No. 2, May 1981, pp. 201-203. (3 pages).
M. Beltramini et al., "Copper Transfer Between Neurospora Copper Metallothionein and Type 3 Copper Apoproteins," FEBS Letters, vol. 142, No. 2, Jun. 1982, pp. 219-222. (4 pages).
M. Beltramini et al., "Spectroscopic Studies on Neurospora Copper Metallothionein," Biochemistry 1983, vol. 22, pp. 2043-2048. (6 pages).
M. Beltramini et al., "Metal Substitution of Neurospora Copper Metallothionein," Biochemistry 1984, vol. 23, pp. 3422-3427. (6 pages).

K. Munger et al., "(Cu,Zn)—Metallothioneins from Fetal Bovine Liver," The Journal of Biological Chemistry, vol. 260. No. 18, Issue of Aug. 25, 1985, pp. 10032-10038. (7 pages).
M. Beltramini et al., "Primary Structure and Spectroscopic Studies of Neurospora Copper Metallothionein," Environmental Health Perspectives, vol. 65, pp. 21-27, 1986, pp. 21-27. (7 pages).
J. Byrd et al., "Characterization of the Copper-Thiolate Cluster in Yeast Metallothionein and Two Truncated Mutants*," The Journal of Biological Chemistry, vol. 263, No. 14, Issue of May 15, 1988, pp. 6688-6694. (7 pages).
M. Beltramini et al., "Luminescence emission from Neurospora copper metallothionein," Biochem. J. (1989) 260, pp. 189-193. (5 pages).
S. Narula et al., "Establishment of the Metal-to-Cysteine Connectivities in Silver-Substituted Yeast Metallothionein," J. Am. Chem. Soc. 1991, vol. 113, pp. 9354-9358. (5 pages).
S. Narula et al., Copper- and Silver-Substituted Yeast Metallothioneins: Sequential H NMR Assignments Reflecting Conformational Heterogeneity at the C Terminus, Biochemistry 1993, vol. 32, pp. 6773-6787. (15 pages).
Z. Gasyna et al., "Luminescence Decay from Copper(I) Complexes of Metallothionein," Inorganica Chimica Acta, vol. 153 (1988), pp. 115-118. (4 pages).
Fred E. Lytle, "Solution Luminescence of Metal Complexes," Applied Spectroscopy, Review Papers, vol. 24, No. 3, 1970, pp. 319-326. (8 pages).
J. H. Anglin, Jr., et al., "Fluorescence of Cu, Au and Ag Mercaptides," Photochemistry and Photobiology, 1971, vol. 13., pp. 279-281. (3 pages).
H. Kuiper et al., "Luminescence of the Copper-Carbon Monoxide Complex of Neurospora Tyrosinase," FEBS Letters, vol. 111, No. 1, Feb. 1980, pp. 232-234. (3 pages).
H. Kuiper et al., "Luminescence of carbon monoxide hemocyanins," Proc. Natl. Acad. Sci. USA, Biochemistry, vol. 77, No. 5, May 1980, pp. 2387-2389. (3 pages).
F. Sabin et al., "Photophysical Properties of Hexanuclear Copper( I) and Silver(1) Clusters," Inorg. Chem., vol. 31, 1992, pp. 1941-1945. (5 pages).
P. Ford et al., "Photochemical and Photophysical Properties of Tetranuclear and Hexanuclear Clusters of Metals with d10 and s2 Electronic Configurations," Acc. Chem. Res., vol. 26, 1993, pp. 220-226. (7 pages).
Prutz et al., "Interaction of copper(I) with nucleic acids," International Journal of Radiation Biology, vol. 58, No. 2, 1990, pp. 215-234. (11 pages).
V. Rostovtsev et al., A Stepwise Huisgen Cycloaddition Process: Copper(I)—Catalyzed Regioselective "Ligation" of Azides and Terminal Alkynes, Angew. Chem. Int. Ed. 2002, vol. 41, No. 14, pp. 2596-2599. (4 pages).
Peter A. Zimmerman et al., Diagnosis of Malaria by Magnetic Deposition Microscopy, American Journal of Tropical Medicine and Hygiene, 2006, vol. 74, No. 4, pp. 568-572. (5 pages).
Stephan Karl et al., Enhanced detection of gametocytes by magnetic deposition microscopy predicts higher potential for Plasmodium falciparum transmission, Malaria Journal, 2008, vol. 7, No. 66. (9 pages).
Megan McNulty et al., Evidence that a coppermetallothionein complex is responsible for fluorescence in acid-secreting cells of the Drosphilla stomach, Cell and Tissue Research, Jun. 2001, vol. 304, Issue 3, pp. 383-389.

* cited by examiner (A)

(B)  P-P section (C)  Q-Q section (a)

(b)

CELL NUCLEUS OBSERVATION SUBSTRATE AND CELL NUCLEUS OBSERVATION APPARATUS

CROSS REFERENCES TO RELATED APPLICATIONS

The present application is a national stage of International Application No. PCT/JP2011/007293 filed on Dec. 27, 2011 and claims priority to Japanese Patent Application No. 2011-005240 filed on Jan. 13, 2011, the disclosure of which is incorporated herein by reference.

BACKGROUND

The present invention relates to a cell nucleus observation substrate and a cell nucleus observation apparatus. More particularly, the present invention relates to a cell nucleus observation substrate for fluorescence staining and morphological observing cell nuclei.

In the related art, cell nuclei of cells, microorganisms and the like have been observed using a microscope and the like, and types and properties of the cells and the microorganisms have been determined based on the morphology of the nuclei. For ease of the morphological observation of the nuclei, a pigment for staining the nuclei is used to stain the cells, the microorganisms and the like prior to the observation.

For example, Non-Patent Documents 1 and 2 describe a technology that erythrocytes are stained by Giemsa to observe the cells infected by malaria parasite. In the apparatuses described in Non-Patent Documents 1 and 2, erythrocytes infected by malaria parasite in blood are collected using a magnet, whereby malaria diagnosis can be done conveniently and speedy.

As the pigment for staining the nuclei, methylene blue that is a blue pigment used for the above-mentioned Giemsa stain, hematoxylin that is a blue purple pigment and the like have been used from the past, for example. In recent years, fluorescent pigments bonding to nucleic acids are used to stain the nuclei. Examples of the fluorescent pigments include Hoechst and DAPI.

In relation to the present invention, conventionally known fluorescence as autofluorescence shown by cells upon a fluorescence observation will be described. One of the fluorescence is orange-colored autofluorescence shown by UV-irradiated cells in the presence of copper. For example, it is reported that cells of a particular part of a *drosophila* larvae midgut emits orange-colored fluorescence when copper is added (see Non-Patent Documents 3 to 11). The cells where the orange-colored fluorescence is especially strongly observed in the *drosophila* larvae midgut are called as "copper cells" or the like. It is reported that the fluorescence is observed at cells around the copper cells (Non-Patent Document 6) and an entire body wall of the larvae (Non-Patent Document 4) when the concentration of the copper added is increased.

There is a description that the above-mentioned orange-colored fluorescence is observed at both cytoplasms and cell nuclei in cells, and, in particular, is detected predominantly in grains of the cytoplasms (see Non-Patent Documents 4 to 6 and 9). There is a description that a wavelength range of fluorescence is 590 to 630 nm, a peak wavelength is 610 nm and a maximum excitation wavelength is 340 nm (see Non-Patent Document 5).

Also for organisms other than *drosophila*, autofluorescence having similar properties is observed. For example, there is reported that orange-colored fluorescence (having a peak wavelength of 605 nm) is observed in an individual liver to which copper is added by UV excitation (excitation wavelength of 310 nm) in rat experiments (see Non-Patent Document 11). Furthermore, there is reported that similar fluorescence is observed in a kidney of a model rat having a kidney and a liver where copper is accumulated with aging (see Non-Patent Document 12). Also, the autofluorescence having similar properties is reported in yeast (see Non-Patent Document 13) and human liver tissues of a Wilson's disease patient (see Non-Patent Document 14). The Wilson's disease is a genetic disorder of insufficient excretion of copper and accumulation of copper in liver cells.

As the above-described fluorescent substance emitting orange-colored fluorescence, a composite of copper and metallothionein (MT) (hereinafter abbreviated to as "Cu-MT") is presumed (see Non-Patent Documents 16 to 25). The Cu-MT has wavelength properties such as an excitation wavelength of 305 nm and a fluorescence wavelength of 565 nm in Non-Patent Document 15, and an excitation wavelength of 310 nm and a fluorescence wavelength of 570 nm in Non-Patent Document 19. It is conceivable that the Cu-MT contain monovalent copper ions (Cu(I)) (see Non-Patent Documents 15, 17, 19, 21 and 25).

As the fluorescent substance containing copper, a compound containing pyrimidine or mercaptide that emits fluorescence by interacting pyrimidine or mercaptide with copper is widely known (see Non-Patent Documents 26 to 31).

On the other hand, an interaction of various metal ions with nucleic acids has been traditionally studied. For example, it is known that when monovalent copper ions are interacted with nucleic acids, a minor amount of copper contained in cell nuclei stabilizes a nucleic acid structure, but hurts DNAs under coexistence of hydrogen peroxide (see Non-Patent Document 32). It is also reported that an interaction with copper changes an absorption spectrum of DNAs (see Non-Patent Documents 32 and 33). Further, it is reported that the change in the absorption spectrum depends on base sequences (specifically, a polymer having a G-C pair and a polymer having an A-T pair) of the DNAs (see Non-Patent Document 32).

Non-Patent Document 1: "Diagnosis of malaria by magnetic deposition microscopy." Am. J. Trop. Med. Hyg., 2006, Vol. 74, No. 4, p. 568-572

Non-Patent Document 2: "Enhanced detection of gametocytes by magnetic deposition microscopy predicts higher potential for Plasmodium falciparum transmission." Malaria Journal, 2008, 7, 66

Non-Patent Document 3: Physiological genetic studies on copper metabolism in the genus *Drosophila*. (1950) Genetics 35, 684-685

Non-Patent Document 4: Organization and function of the inorganic constituents of nuclei. (1952) Exp. Cell Res., Suppl. 2:161-179

Non-Patent Document 5: Ultrastructure of the copper-accumulating region of the *Drosophila* larval midgut. (1971) Tissue Cell. 3, 77-102

Non-Patent Document 6: Specification of a single cell type by a *Drosophila* homeoticgene. (1994) Cell. 76, 689-702

Non-Patent Document 7: Two different thresholds of wingless signalling with distinct developmental consequences in the *Drosophila* midgut. (1995) EMBO J. 14, 5016-5026.

Non-Patent Document 8: Calcium-activated potassium channel gene expression in the midgut of *Drosophila*. (1997) Comp. Biochem. Physiol. B Biochem. Mol. Biol. 118, 411-420

Non-Patent Document 9: Evidence that a copper-metallothionein complex is responsible for fluorescence in acid-secreting cells of the *Drosophila* stomach. (2001) Cell Tissue Res. 304, 383-389

Non-Patent Document 10: Peptidergic paracrine and endocrine cells in the midgut of the fruit fly maggot. (2009) Cell Tissue Res. 336, 309-323

Non-Patent Document 11: A luminescence probe for metallothionein in liver tissue:emission intensity measured directly from copper metallothionein induced in ratliver. (1989) FEBS Lett. 257, 283-286

Non-Patent Document 12: Direct visualization of copper-metallothionein in LEC rat kidneys: application of autofluorescence signal of copper-thiolate cluster. (1996) J. Histochem. Cytochem. 44, 865-873

Non-Patent Document 13: Incorporation of copper into the yeast Saccharomyces cerevisiae. Identification of Cu(I)-metallothionein in intact yeast cells. (1997) J. Inorg. Biochem. 66, 231-240

Non-Patent Document 14: Portmann B. Image of the month. Copper-metallothionein autofluorescence. (2009) Hepatology. 50, 1312-1313

Non-Patent Document 15: Luminescence properties of *Neurospora* copper metallothionein. (1981) FEBS Lett. 127, 201-203

Non-Patent Document 16: Copper transfer between *Neurospora* copper metallothioneinand type 3 copper apoproteins. (1982) FEBS Lett. 142, 219-222

Non-Patent Document 17: Spectroscopic studies on *Neurospora* copper metallothionein. (1983) Biochemistry. 22, 2043-2048

Non-Patent Document 18: Metal substitution of *Neurospora* copper metallothionein. (1984) Biochemistry. 23, 3422-3427

Non-Patent Document 19: (Cu,Zn)-metallothioneins from fetal bovine liver. Chemical and spectroscopic properties. (1985) J. Biol. Chem. 260, 10032-10038

Non-Patent Document 20: Primary structure and spectroscopic studies of *Neurospora* copper metallothionein. (1986) Environ. Health Perspect. 65, 21-27

Non-Patent Document 21: Characterization of the copper-thiolate cluster in yeast metallothionein and two truncated mutants. (1988) J. Biol. Chem. 263, 6688-6694

Non-Patent Document 22: Luminescence emission from *Neurospora* copper metallothionein. Time-resolved studies. (1989) Biochem J. 260, 189-193

Non-Patent Document 23: Establishment of the metal-to-cysteine connectivities in silver-substituted yeast metallothionein (1991) J. Am. Chem. Soc. 113, 9354-9358

Non-Patent Document 24: Copper- and silver-substituted yeast metallothioneins: Sequential proton NMR assignments reflecting conformational heterogeneity at the Cterminus. (1993) Biochemistry. 32, 6773-6787

Non-Patent Document 25: Luminescence decay from copper (I) complexes of metallothionein. (1998) Inorg. Chim. Acta. 153, 115-118

Non-Patent Document 26: Solution Luminescence of Metal Complexes. (1970) Appl. Spectrosc. 24, 319-326

Non-Patent Document 27: Fluorescence of Cu, Au and Ag mercaptides. (1971) Photochem. Photobiol. 13, 279-281

Non-Patent Document 28: Luminescence of the copper-carbon monoxide complex of *Neurospora* tyrosinase. (1980) FEBS Lett. 111, 232-234

Non-Patent Document 29: Luminescence of carbon monoxide hemocyanins. (1980) Proc. Natl. Acad. Sci. U.S.A. 77, 2387-2389

Non-Patent Document 30: Photophysical properties of hexanuclear copper(I) and silver(I) clusters. (1992) Inorg. Chem., 31, 1941-1945

Non-Patent Document 31: Photochemical and photophysical properties of tetranuclear and hexanuclear clusters of metals with d10 and s2 electronic configurations. (1993) Acc. Chem. Res. 26, 220-226

Non-Patent Document 32: Interaction of copper(I) with nucleic acids. (1990) Int. J. Radiat. Biol. 58, 215-234

Non-Patent Document 33: Copper(I)-Catalyzed Regioselective "Ligation" of Azides and Terminal Alkynes. (2002) Ang. Chem. Int. Ed. 41, 2596-2599

SUMMARY

Problem to be Solved by the Invention

In a method of observing cell nuclei by nuclear staining using a conventional pigment, it is required to fix cells, microorganisms and the like, repeat immersion to a pigment solution and cleaning, drying and so on. Therefore, it requires much effort and time. Working proficiencies are required.

A main object of the present invention is to provide a technology of staining nuclei of cells, microorganisms and the like by a simple operation and observing their forms.

Means for Solving the Problem

The present inventors have discovered that nucleic acids that are contacted with copper will emit fluorescence by irradiating with light in ultraviolet wavelength region, and have devised a cell nucleus observation substrate and the like according to the present invention by applying the discovery.

In other words, in order to solve the problem, the present invention provides a cell nucleus observation substrate including an introduction part into which a sample liquid containing cells is introduced, and an observation area within which the cells in the sample liquid introduced from the introduction part is held, copper being disposed on a flow path of the sample liquid in the introduction part and the observation area so that the copper being capable of contacting with the sample liquid.

In the cell nucleus observation substrate, when the cell in the sample liquid introduced from the introduction part is contacted with copper, a nucleic acid therein will emit fluorescence and is held within the observation area. Accordingly, in the cell nucleus observation substrate, the cell including the nucleus being fluorescence stained can be observed at the observation area.

In the cell nucleus observation substrate, the copper is preferably formed and disposed on the flow path.

The cell nucleus observation substrate may include a magnet that is disposed attachably and detachably and forms a magnetic field within the observation area, and the cells in the sample liquid flowing through the flow path are held within the observation area based on a magnetic force. In addition, in the cell nucleus observation substrate, the observation area is disposed in a space between two opposing substrates at a predetermined distance. The cell nucleus observation substrate includes an introduction part where the sample liquid is introduced into the space, and an absorption member that absorbs the sample liquid introduced from the introduction part to the space, in which the magnet is attached at a position between the introduction part and the absorption member.

Furthermore, the present invention provides a cell nucleus observation apparatus including an introduction part into which a sample liquid containing cells is introduced, an observation area within which the cells in the sample liquid introduced from the introduction part are held, a substrate where copper is disposed on a flow path of the sample liquid in the introduction part and the observation area so that the copper being capable of contacting with the sample liquid, and an optical detecting means for irradiating a light to the observation area and detecting fluorescence generated.

In the cell nucleus observation apparatus, when the cell in the sample liquid introduced from the introduction part is contacted with copper, a nucleic acid therein will emit fluorescence and is held within the observation area. Accordingly, in the cell nucleus observation apparatus, the observation area is irradiated with the light, and the fluorescence generated is detected, whereby a nuclear fluorescence staining image of the cells can be observed.

In the cell nucleus observation apparatus, a wavelength of the light irradiated by the optical detecting means is 300 to 420 nm.

Effect of the Invention

The present invention provides a technology of staining nuclei of cells, microorganisms and the like by a simple operation and observing their forms.

Additional features and advantages are described herein, and will be apparent from the following Detailed Description and the figures.

DETAILED DESCRIPTION

Figure 1:
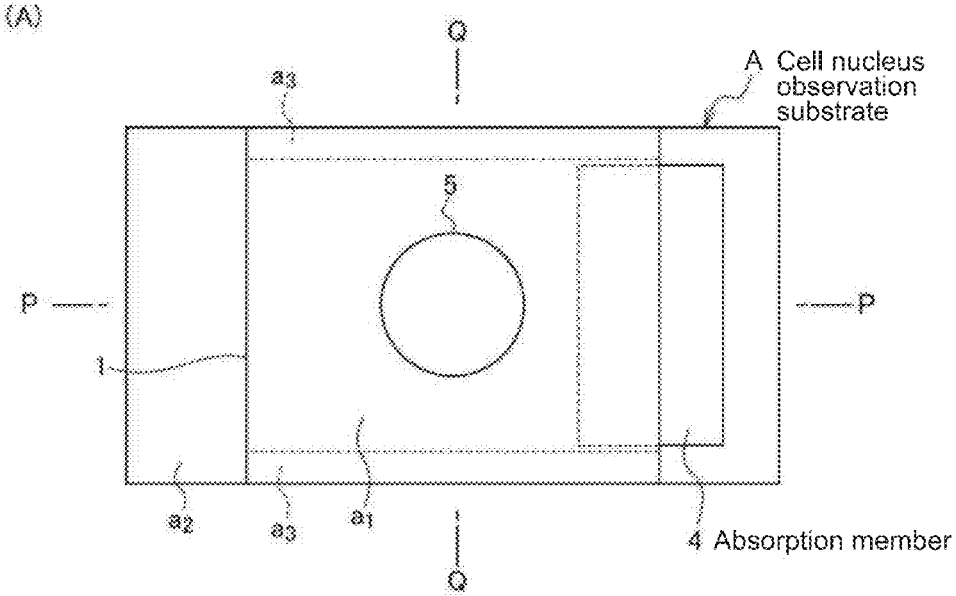
FIG. 1 A schematic diagram of illustrating a configuration of a cell nucleus observation substrate according to a first embodiment of the present invention.
Figure 1:
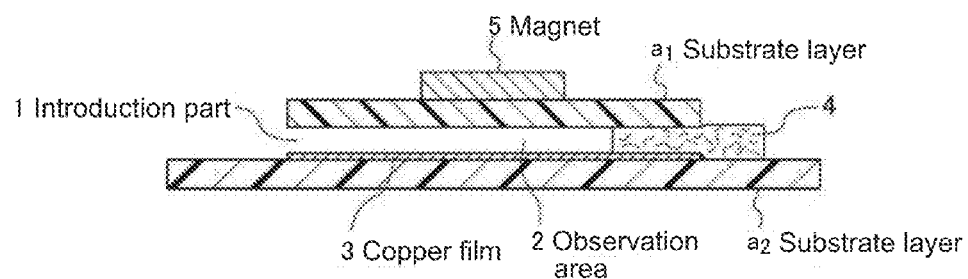
Figure 1:
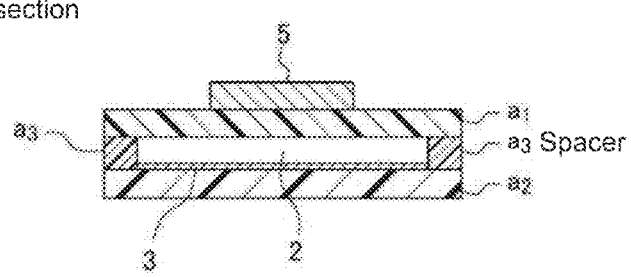

Hereinafter, embodiments according to the present technology will be described with reference to the drawings. The embodiments described below are provided for purposes of illustration only, and merely depict typical embodiments of the present technology, and the scope of the present technology should not be construed narrower. The embodiments will be described in the following order.
1. Cell Nucleus Observation Substrate
(1) First Embodiment
(2) Second Embodiment
2. Cell Nucleus Observation Apparatus 1. Cell Nucleus Observation Substrate (1) First Embodiment FIG. 1 is a schematic diagram of illustrating a configuration of a cell nucleus observation substrate according to a first embodiment of the present invention. (A) is a top view, (B) is a sectional view corresponding to a P-P section in (A), and (C) is a sectional view corresponding to a Q-Q section in (A).

In the Figure, a cell nucleus observation substrate designated in a symbol A includes a substrate layer $a_1$ and a substrate layer $a_2$. The substrate layer $a_1$ faces to the substrate layer $a_2$ at a predetermined space via a spacer $a_3$. The space has a non-limiting thickness, but the thickness is desirably from several micrometers to hundreds micrometers, preferably about 10 to 50 micrometers. At a part of the space between the substrate layer $a_1$ and the substrate layer $a_2$, an observation area 1 is disposed as an observation site of cells.

A part of the space formed by the substrate layer $a_1$ and the substrate layer $a_2$ is closed by the spacer $a_3$, and the rest thereof is open and is communicated with exterior. Specifically, upper and lower two sides of the space formed by the substrate layer $a_1$ and the substrate layer $a_2$ is closed by the spacer $a_3$, and left and right two sides of the space is communicated with exterior in FIG. (A). A part of the open space between the substrate layer $a_1$ and the substrate layer $a_2$ (in FIG. (A), a left side) is an introduction part 1 of a sample liquid to the observation area 2 disposed at the space. At a part of the open space (in FIG. (A), a right side) on the opposite side of the introduction part 1, an absorption member 4 that absorbs the sample liquid introduced to the space from the introduction part 1 is inserted into and disposed between the substrate layer $a_1$ and the substrate layer $a_2$. The sample liquid introduced from the introduction part 1 migrates the space between the substrate layer $a_1$ and the substrate layer $a_2$, and is absorbed by the absorption member 4, whereby the cells contained in the sample liquid are held within the observation area 2.

As the sample liquid, a buffer liquid containing a salt such as sodium chloride (NaCl), potassium chloride (KCl), magnesium chloride ($MgCl_2$) is preferably used (see Example 2 later). One salt or two or more of salts may be contained, and the concentration thereof is not especially limited. Preferably, the concentration is set to 0.025 M or more. The buffer for use in the sample liquid may not contain a cheating agent for Cu(II) ions (see Example 2). For the purpose of decreasing a damage to cells, the buffer liquid that is adjusted to have a salt concentration almost being isotonic to physiological tissues and cells (for example, physiological saline) is desirably used as the sample liquid. As the buffer liquid, phosphoric buffer physiological saline (PBS) using phosphoric buffer may be used (see Example 2).

The absorption member 4 is not especially limited as long as the sample liquid can be absorbed, and may be, for example, filter paper, absorption fiber and absorption resin.

On the surface of the substrate layer $a_2$ facing to the substrate layer $a_1$, a copper film 3 is formed. The cells in the sample liquid introduced from the introduction part 1 migrates the space between the substrate layer $a_1$ and the substrate layer $a_2$ while contacting with the copper eluted into the sample liquid. In this case, when nucleic acids are contacted with copper, the nucleic acids in cell nuclei will emit fluorescence by irradiating with light in ultraviolet wavelength region.

The copper film 3 is formed by sputtering or vapor deposition on a surface of the substrate using a conventionally known method. A thickness of the copper film 3 is not especially limited, but is several nms to several tens nms, preferably about 20 to 40 nm. Within the film thickness range, the copper film 3 has a light permeability. It is therefore possible to irradiate a light or detect fluorescence permeating through the copper film 3, when the cells held within the observation area 2 are irradiated with the light and a nuclear fluorescence staining image of the cells is observed. The light irradiation and the fluorescence detection can be done at a surface opposite to the copper film 3 using an incident-light optical system. In this case, the copper film may not have light permeability.

In the Figure, reference numeral 5 designates a magnet for forming a magnetic field within the observation area 2. The magnet 5 is disposed on the substrate layer $a_1$ adjacent to its surface opposite to the observation area 2. The magnet 5 may be disposed attachably and detachably at either side of the substrate layer $a_1$ and the substrate layer $a_2$. The magnet 5 selects, concentrates and holds the cells in the sample liquid, which migrate the space between the substrate layer $a_1$ and the substrate layer $a_2$, within the observation area 2 based on a magnetic force of the magnetic field formed within the observation area 2. In this way, only the cells adsorbed to a magnetic substance can be accumulated within the observation area 2.

A material of the magnet 5 is not especially limited as long as the magnetic field can be formed within the observation area 2, and can be a neodymium magnet, a samarium-cobalt magnet or a ferrite magnet, for example. Also, a position of the magnet 5 is not limited as long as the magnetic field can be formed within the observation area 2, and may be buried into the substrate layer $a_1$ or the substrate layer $a_2$. In the cell nucleus observation substrate according to the present invention, the magnet 5 will not be an essential constituent.

The cells accumulated within the observation area 2 are in the state that nucleic acids within the cell nuclei emit fluorescence once they are in contact with copper and are irradiated with ultraviolet rays. Accordingly, the observation area 2 is irradiated with ultraviolet rays and fluorescence generated is detected, thereby observing the nuclear fluorescence staining image of the cells.

A wavelength of the light to be irradiated is preferably 300 to 420 nm. As the material of the substrate layer $a_1$ and the substrate layer $a_2$, a material having light permeability, less autofluorescence, and less optical error due to a small wavelength distribution is preferably selected in order to permeate the light to be irradiated to the observation area 2 and fluorescence generated from the cell nuclei. As the material of the substrate layer $a_1$ and the substrate layer $a_2$, glass and various plastics (polypropylene, polycarbonate, cycloolefin polymer, polydimethyl siloxane etc.) can be used. In addition, in order that the light irradiated to the observation area 2 and the fluorescence generated from the cell nuclei are prevented from blocking by the magnet 5, the magnet 5 disposed on the substrate layer $a_1$ can be removed when the nuclear fluorescence staining image is observed. Alternatively, using an incident-light optical system, the light irradiation and the fluorescence can be observed from the surface opposite to the magnet.

As described above, in the cell nucleus observation substrate A, the cells having magnetism in the sample liquid introduced from the introduction part 1 are accumulated within the observation area 2 and are contacted with the copper film 3 to be in the state that nucleic acids within the cell nuclei emit fluorescence, whereby the nuclear fluorescence staining image of the cells can be observed. Accordingly, in the cell nucleus observation substrate A, the cell nuclei can be fluorescence stained by a simple operation and can be observed their forms without requiring fixing cells, microorganisms and the like, repetitive immersion to a pigment solution and cleaning, drying and so on that are required in the cell nucleus observation method by nuclear staining using conventional pigments including the Giemsa stain.

In particular, in the cell nucleus observation substrate A, as the cells can be accumulated within the observation area 2 by the magnet 5, and can be observed, it is suitable for nucleus observation of the cells having magnetism. Examples of the cells having magnetism include cells labeled with magnetic labeled antibodies and malaria parasite cells that erythrocytes are infected as described in the above-mentioned Non-patent documents 1 and 2.

In the cell nucleus observation substrate A, when the sample liquid containing the cells provided by labeling a specific cell population with magnetic labeled antibodies is used, only the specific cell population can be accumulated within the observation area 2 based on a magnetic action between the magnet 5 and the magnetic labeled antibodies. Accordingly, the nuclei can be observed by concentrating only leucocytes in a blood sample, which can be used for diagnosis of leukemia based on a nucleus shape or of allergy based on eosinophil counts. The specific cell population can be labeled using the magnetic labeled antibodies specifically bonded to specific cell surface antigens. It is also possible that an antibody labeling area is disposed between the introduction part 1 and the observation area 2, and the magnetic labeled antibodies are mixed with the cells in the antibody labeling area.

In addition, in erythrocytes infected by malaria parasite, it is known that a magnetic substance called Hemozoin is formed. In the cell nucleus observation substrate A, when a blood sample collected from a malaria patient is used, only the erythrocytes infected by malaria parasite can be accumulated within the observation area 2 based on the magnetic action between the magnet 5 and Hemozoin. Accordingly, the erythrocytes infected with the malaria parasite in the blood sample can be concentrated to observe malaria parasite nuclei. It is possible that malaria infection and a malaria parasite type can be easily and accurately determined. In this case, in the cell nucleus observation substrate A, the nuclear fluorescence staining image can be observed and determined without requiring fixing, staining, drying and so on different from malaria diagnosis by the conventional Giemsa stain.

As the malaria parasite, tropical malaria parasite, tertian malaria parasite, quartan malaria parasite, oval malaria parasite or the like is known. In addition, as a growing stage of a parasite body, ringform, trophozoite, schizont, gametocyte or the like is known. It is very important to adequately identify the type and the growing stage of the parasite for deciding a therapeutic strategy of the infected patient.

In the cell nucleus observation substrate A as described above, the case that the copper film 3 is formed on the surface of the substrate layer $a_2$ facing to the substrate layer $a_1$ is described as an example. In the cell nucleus observation substrate A, the copper film 3 may be formed at any area of a flow path of the sample liquid in the introduction part 1 and the observation area 2 so that the copper film 3 can be in contact with the sample liquid. For example, the copper film 3 may be formed at a part of or entire surface of the substrate layer $a_1$. In the cell nucleus observation substrate according to the present invention, copper may be disposed as not only a film but as powder, fine particles, wire, plate and foil. In addition, in the cell nucleus observation substrate according to the present invention, copper is preferably a solid state from a standpoint that the substrate is stably stored. However, a copper solution may be used. When the copper solution is used, it is preferable that a reducing agent is mixed therewith in order to maintain the state that dissolved Cu ions are reduced from divalent cation to monovalent cation. As the reducing agent, sodium ascorbate can be used as described later (see Example 1). According to the present invention, the term "copper" involves a copper metal and a copper alloy.

(2) Second Embodiment

Figure 2:
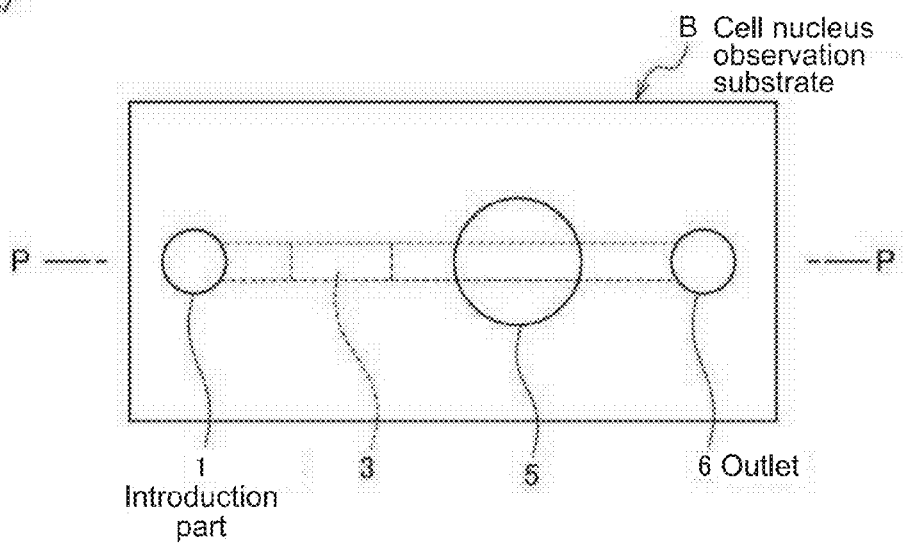
FIG. 2 A schematic diagram of illustrating a configuration of a cell nucleus observation substrate according to a second embodiment of the present invention.
Figure 2:
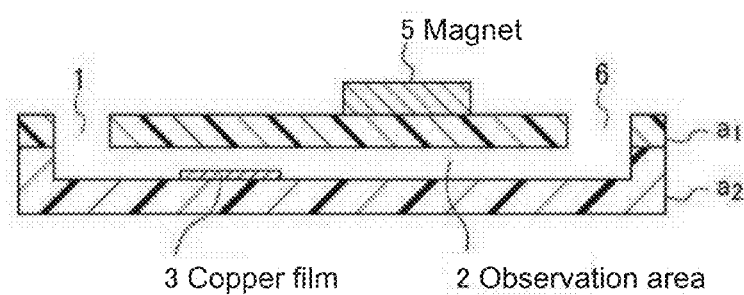

FIG. 2 is a schematic diagram of illustrating a configuration of a cell nucleus observation substrate according to a second embodiment of the present invention. (A) is a top view, (B) is a sectional view corresponding to a P-P section in (A).

In the Figure, a cell nucleus observation substrate designated by a symbol B is configured by adhering the substrate layer $a_1$ and the substrate layer $a_2$. In the substrate layer $a_1$, the introduction part 1 into which the sample liquid is introduced and an outlet 6 from which the sample liquid is discharged are formed. On the substrate layer $a_2$, a flow path for passing the sample liquid introduced from the introduction part 1. At a part of the flow path, the observation area 2 is disposed as a site for observing the cells.

A liquid feeding means (not shown) is connected to the introduction part 1 and the outlet 6. The sample liquid introduced from the introduction part 1 passes through the flow path, and is discharged from the outlet 6. The liquid feeding means is configured of a general-purpose pump, tube, sample liquid tank, waste tank or the like. In addition, the liquid feeding means may include a configuration that the sample liquid is introduced, fed and discharged utilizing centrifugal force or gravity.

On a surface of the flow path formed on the substrate layer $a_2$, the copper film 3 is formed. The copper film 3 may be fully formed over the flow path surface. Alternatively, the copper film 3 may be formed partly at the surface of the flow path of the sample liquid in an upstream flow direction not at the observation area 2, as shown in the Figure. Or, the copper film 3 may be disposed on the substrate layer $a_1$. The cells in the sample liquid introduced from the introduction part 1 to the flow path are contacted with the copper film 3 or copper eluted from the copper film 3, and flow into the observation area 2. In this case, the nucleic acids in the cell nuclei that are contacted with copper will emit fluorescence by irradiating with ultraviolet rays.

The copper film 3 is formed by sputtering or vapor deposition on a surface of the substrate using a conventionally known method. A thickness of the copper film 3 is not especially limited, but is several nms to several tens nms, preferably about 20 to 40 nm. Within the thickness range, the copper film 3 has a light permeability. It is therefore possible to irradiate a light or detect fluorescence permeating through the copper film 3, when the cells held within the observation area 2 are irradiated with the light and a nuclear fluorescence staining image of the cells are observed.

In the Figure, reference numeral 5 designates a magnet for forming a magnetic field within the observation area 2. The magnet 5 is disposed attachably and detachably on the substrate layer $a_1$ adjacent to its surface opposite to the observation area 2. The magnet 5 holds the cells in the sample liquid, which are introduced from the introduction part 1 and flow the flow path, within the observation area 2 based on a magnetic force of the magnetic field formed within the observation area 2. In this way, by the magnet 5, the cells that are contacted with copper and will emit fluorescence are accumulated within the observation area 2. As the material of the magnet 5 is similar to that of the cell nucleus observation substrate A in the first embodiment, a description thereof will be herein omitted.

Also in the cell nucleus observation substrate according to this present embodiment, the magnet 5 will not be an essential constituent. As a configuration to accumulate the cells within the observation area 2, a substance for capturing the cells in the sample liquid flowing (for example, an antibody against a cell membrane antigen for capturing specific cells) may be solid-phased, instead of the magnet 5. Alternatively, an electrode for forming an electric field within the observation area 2 is disposed instead of the magnet 5, and the cells may be held within the observation area 2 based on an electrical force.

The cells accumulated within the observation area 2 are in the state that nucleic acids within the cell nuclei emit fluorescence once they are in contact with copper and are irradiated with ultraviolet rays. Accordingly, the observation area 2 is irradiated with ultraviolet rays and fluorescence generated is detected, thereby observing the nuclear fluorescence staining image of the cells.

A wavelength of the light to be irradiated is preferably 300 to 420 nm. As the material of the substrate layer $a_1$ and the substrate layer $a_2$, a material having light permeability, less autofluorescence, and less optical error due to a small wavelength distribution is preferably selected in order to permeate the light to be irradiated to the observation area 2 and fluorescence generated from the light and the cell nuclei. As the material of the substrate layer $a_1$ and the substrate layer $a_2$, glass and various plastics (polypropylene, polycarbonate, cycloolefin polymer, polydimethyl siloxane etc.) can be used. In addition, in order that the light irradiated to the observation area 2 and the fluorescence generated from the cell nuclei are prevented from blocking by the magnet 5, the magnet 5 disposed on the substrate layer $a_1$ can be removed when the nuclear fluorescence staining image is observed. Alternatively, using an incident-light optical system, the light irradiation and the fluorescence can be observed from the surface opposite to the magnet.

As described above, in the cell nucleus observation substrate B, the cells in the sample liquid introduced from the introduction part 1 are in contact with the copper film 3 and accumulated within the observation area 2 to be in the state that nucleic acids within the cell nuclei emit fluorescence, whereby the nuclear fluorescence staining image of the cells can be observed. Accordingly, in the cell nucleus observation substrate B, the cell nuclei can be fluorescence stained by a simple operation and can be observed their forms without requiring fixing cells, microorganisms and the like, repetitive immersion to a pigment solution and cleaning, drying and so on that are required in the cell nucleus observation method by nuclear staining using conventional pigments including the Giemsa stain.

2. Cell Nucleus Observation Apparatus

The cell nucleus observation apparatus according to the present invention includes the above-described cell nucleus observation substrate and an optical detecting means for irradiating a light to the observation area of the substrate, and thus can observe the nuclear fluorescence staining image of the cells. The cell nucleus observation apparatus may be provided by changing a conventionally known fluorescence microscope as appropriate, and includes the following configuration as the optical detecting means.

The light to be irradiated to the observation area has preferably within an ultraviolet region from 300 to 420 nm. As the light source, a laser, an LED or the like can be used. Preferably, a UV-LED having a central wavelength of about 360 nm is used. The light from the light source is guided to the observation area by an optical path configured of an optical filter, a mirror, a lens or the like, as required.

The fluorescence generated from the observation area is detected by an optical detector such as a photo detector, a photo diode, a photo multiplier, a CCD camera, a CMOS camera and the like, and is displayed on an image display apparatus. Alternatively, the fluorescence generated from the observation area may be observed with the naked eye via an ocular lens etc. The fluorescence generated from the observation area is guided by the optical path configured of the optical filter, the mirror, the lens or the like, as required, to the optical detector or the ocular lens. The optical filter used has selectivity to the light having about 600 nm, which is in a fluorescence wavelength region, generated from the nucleic acids contacted with copper (see Example 1 below).

Example 1

Figure 3:
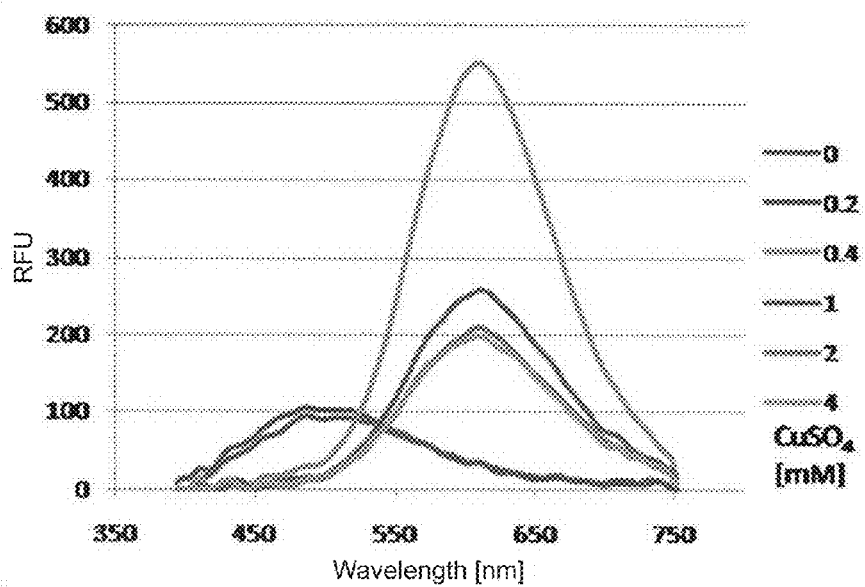
FIG. 3 Graphs each substituting a drawing and showing a fluorescent spectrum and an RFU value obtained by bringing ssDNAs into contact with $CuSO_4$ having a varied concentration under the condition of an S.A. concentration of 50 mM; (A) shows the fluorescent spectrum and (B) shows a peak RFU value (Example 1).
Figure 3:
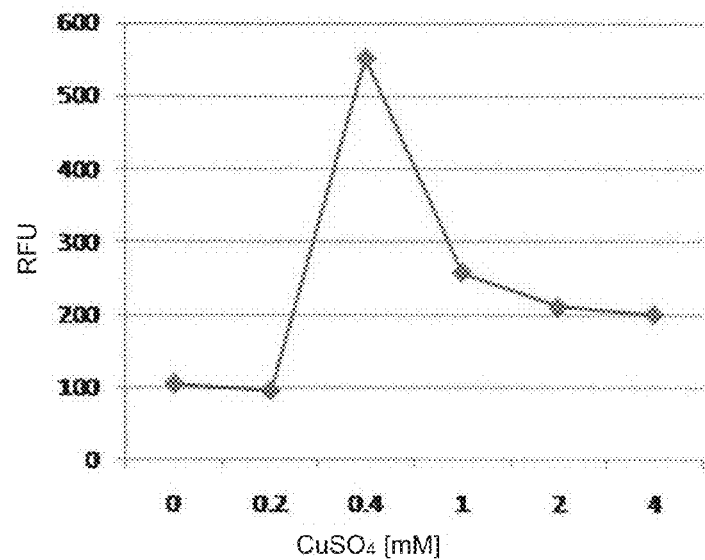
Figure 4:
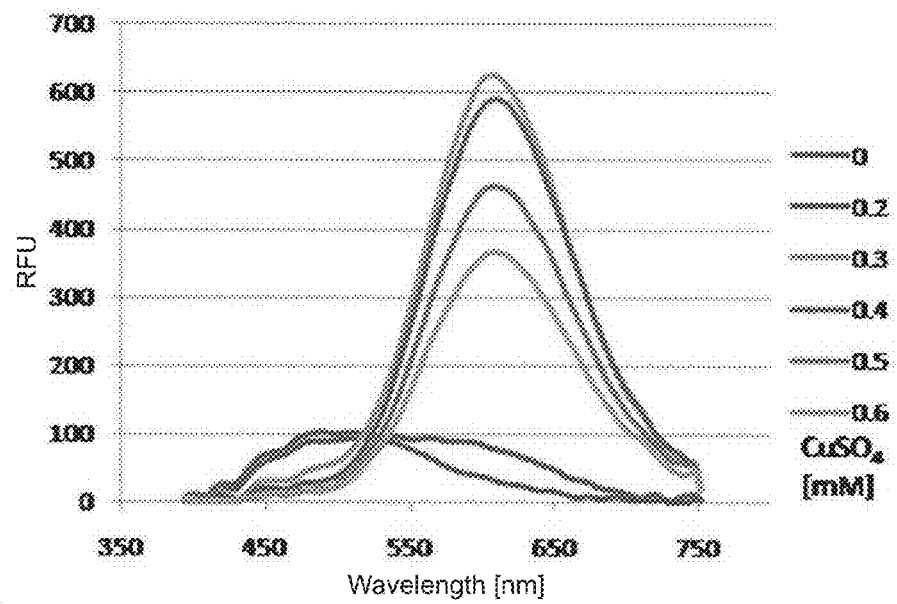
FIG. 4 Graphs each substituting a drawing and showing fluorescent spectra and an RFU value obtained by bringing ssDNAs into contact with $CuSO_4$ having a varied concentration under the condition of an S.A. concentration of 50 mM; (A) shows the fluorescent spectra and (B) shows a peak RFU value (Example 1).
Figure 4:
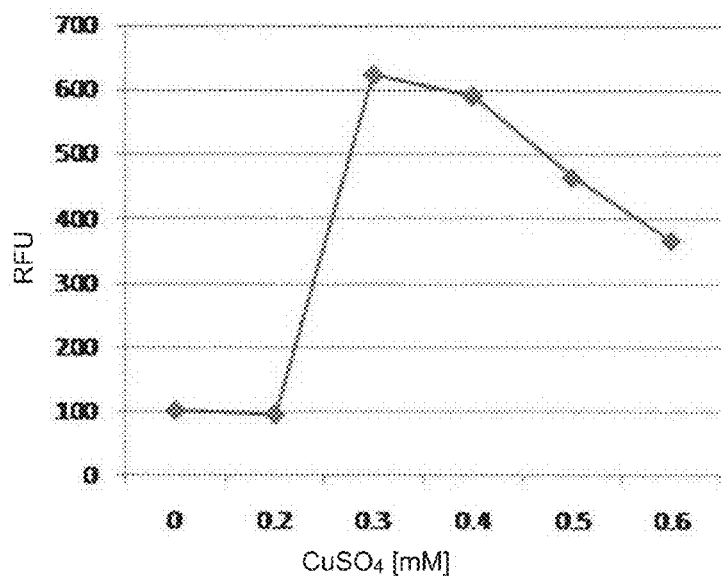
Figure 5:
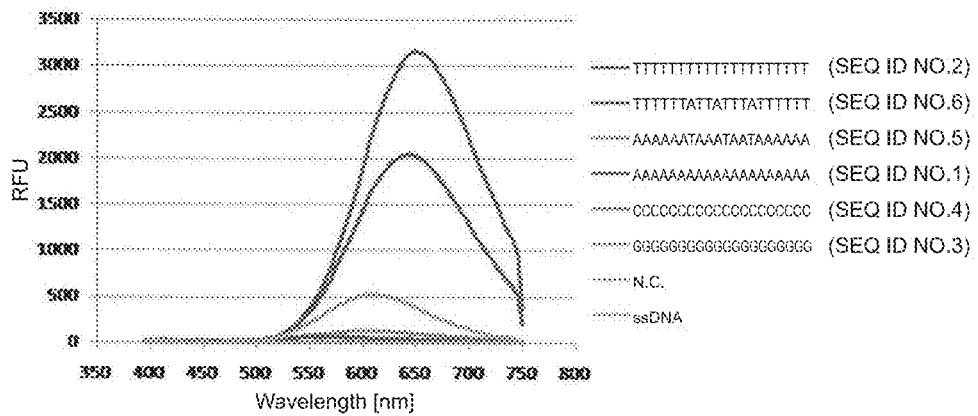
FIG. 5 Graphs each substituting a drawing and showing fluorescent spectra and RFU values obtained by bringing oligo-DNAs into contact with $CuSO_4$ having a concentration of 0.4 mM under the condition of an S.A. concentration of 4 mM (Example 1).
Figure 5:
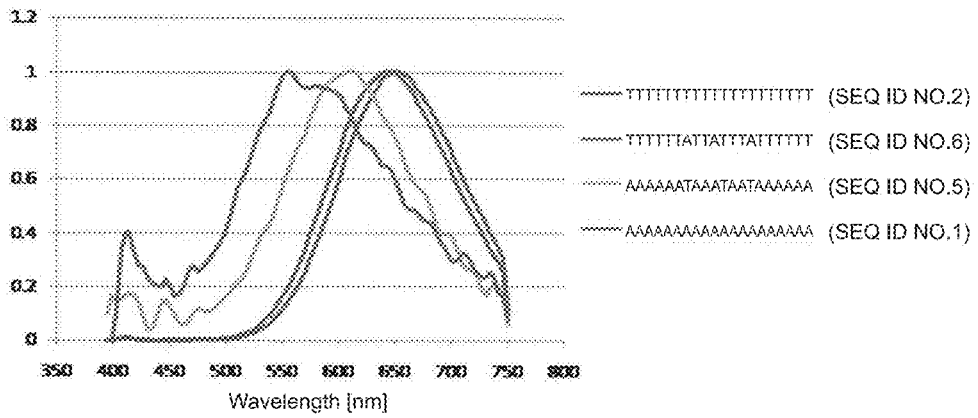
Figure 6:
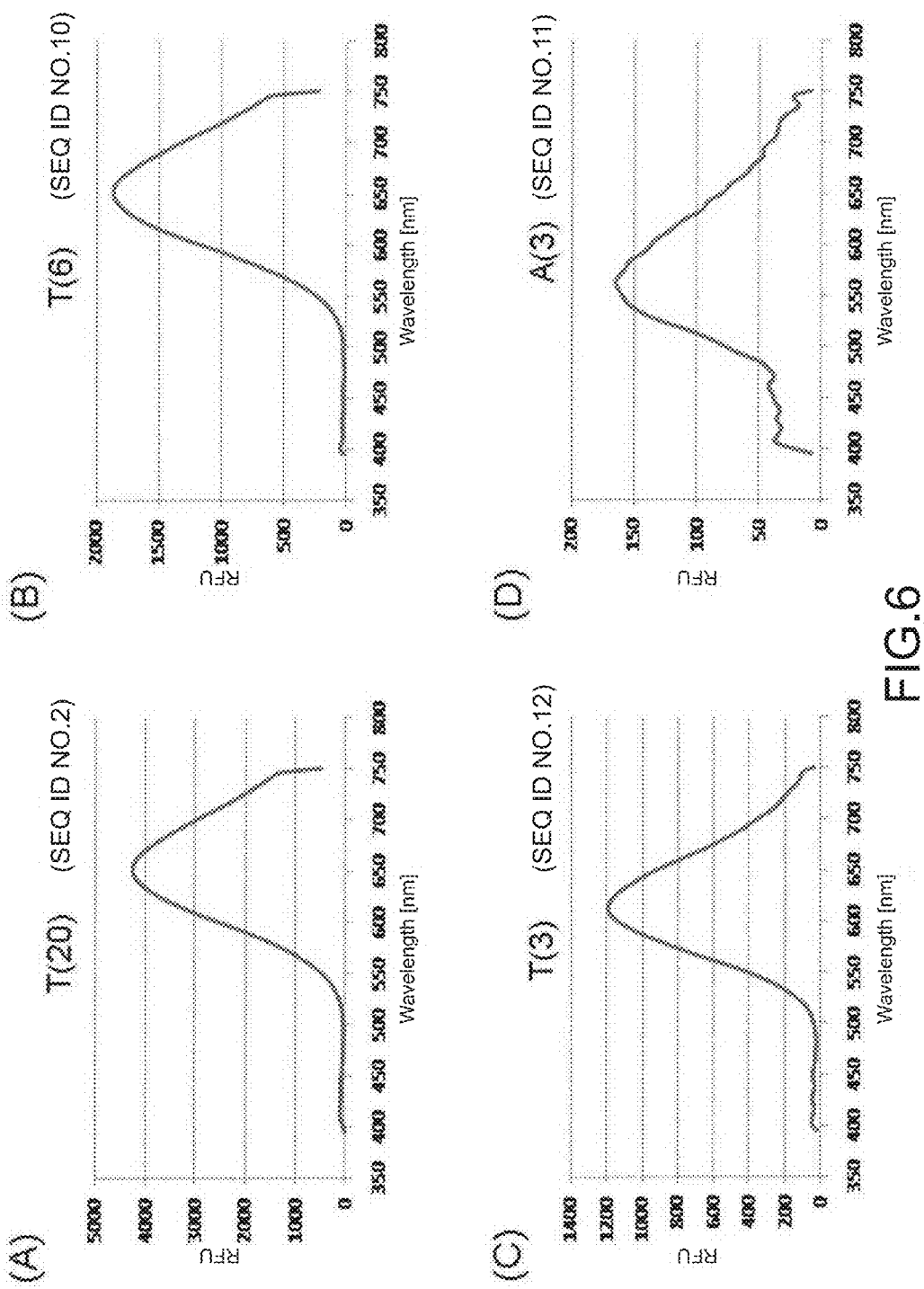
FIG. 6 Graphs each substituting a drawing and showing a fluorescent spectrum and an RFU value obtained by bringing oligo-DNAs into contact with $CuSO_4$ having a concentration of 0.4 mM under the condition of an S.A. concentration of 4 mM (Example 1).

Example 1 illustrates that orange-colored fluorescence was emitted by ultraviolet irradiation under certain conditions when nucleic acids are mixed with a solution including Cu(I) ions generated by reducing Cu(II) ions with an ascorbic acid.
<Material and Method>
Cu: a $CuSO_4$ solution and (+)-Sodium L-ascorbate (hereinafter referred to as "S.A.") were purchased from Sigma-Aldrich.
Nucleic acid: Sonicated Salmon Sperm DNA (hereinafter referred to as "ssDNA") purchased from BioDynamics laboratory Inc. (Tokyo, Japan) was used. In addition, as oligo-DNAs, Custom Oligo purchased from Invitrogen Corporation was used.
Buffer: HEPPSO purchased from DOJINDO Laboratories (Kumamoto, Japan) was used by adjusting the pH to 8.5 pursuant to the protocols provided by the manufacturer.
Fluorcphotometer: NanoDrop 3300 (Thermo Fisher Scientific, Inc., Waltham, Mass., USA) or type F-4500 spectrofluorophotometer (Hitachi High-Technologies Corporation) was used. In the NanoDrop 3300, a UV LED light source was used to provide exciting light. A fluorescent spectrum excited by the exciting light was measured. Using a companion software, Relative Fluorescence Units (RFU) at a wavelength where a spectrum intensity became at maximum was acquired as a peak RFU value. In the type F-4500 spectrofluorophotometer, a quartz capillary and a dedicated adapter cell manufactured by Helix Biomedical Accessories, Inc. were used. Unless otherwise noted below, the NanoDrop 3300 was used.
Spectrophotometer: NanoDrop 1000 Spectrophotometer was used to measure an absorption spectrum.
Sample preparation and fluorescence measurement: 50 mM of a HEPPSO buffer was mixed with sodium chloride (250 mM), $CuSO_4$ (0 to 4 mM), S.A. (4, 50 mM), ssDNAs (1 mg/ml) or oligo-DNAs (50, 250, 500 µM) to provide 20 µl of a sample. It is known that the S.A. has an action to reduce Cu(II) ions generated from $CuSO_4$ in the solution to Cu(I) (see Non-Patent Document 33).
<Results>
FIGS. 3 and 4 are graphs each showing a fluorescent spectrum and an RFU value obtained by changing a concentration of $CuSO_4$ under the condition of an S.A. concentration of 50 mM; (A) shows the fluorescent spectrum and (B) shows a peak RFU value.
FIGS. 5 and 6 are graphs each showing fluorescent spectra obtained under the conditions of $CuSO_4$ having a concentration of 0.4 mM and an S.A. concentration of 4 mM. The oligo-DNAs having base lengths of 20, 10, 6 and 3 had a concentration of 50, 50, 250, and 500 µM, respectively. FIG. 5 shows a result of the oligo DNAs having the base sequences described in SEQ ID NOS. 1 to 6. An abscissa axis represents a wavelength, an ordinate axis in (A) represents the RFU value in each wavelength, and an ordinate axis in (B) represents a value provided by dividing the RFU value in each wavelength by a maximum RFU value. FIG. 6 shows a result (A) of the oligo-DNAs having the base sequences described in SEQ ID NO. 2 (hereinafter described as T(20)), a. result (B) of the oligo-DNAs having the base sequences described in SEQ ID NO. 10 (hereinafter described as T(6)), a result (C) of the oligo-DNAs having the base sequences described in SEQ ID NO. 12 (hereinafter described as T(3)), and a result (D) of the oligo-DNAs having the base sequences described in SEQ ID NO. 11 (hereinafter described as T(3)). Each abscissa axis represents a wavelength, and each ordinate axis represents an RFU value in each wavelength.

As shown in the Figures, it was confirmed that the patterns of the fluorescent spectra (a peak wavelength and an intensity) were changed depending on the base sequences of the nucleic acids.

Figure 7:
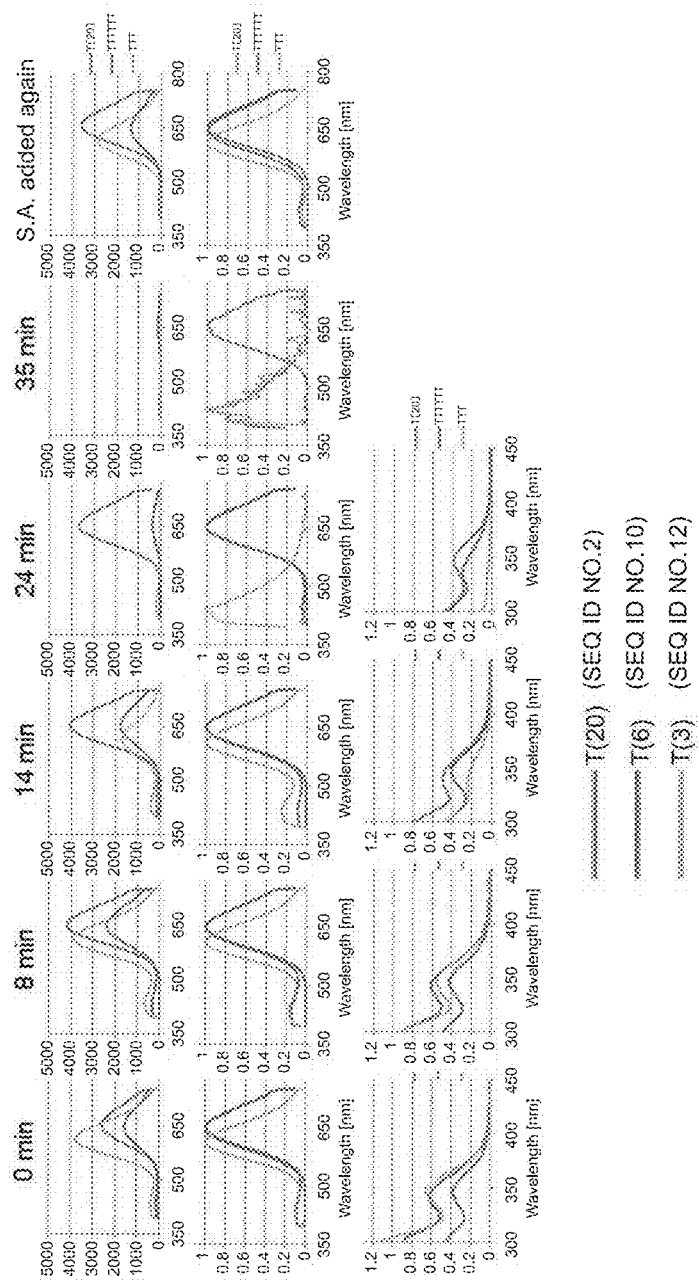
FIG. 7 Graphs each substituting a drawing and showing a change with elapsed time of a fluorescent spectrum and absorption spectra obtained in oligo-DNAs T(20), T(6) and T(3) under the condition of a $CuSO_4$ concentration of 0.4 mM and an S.A. concentration of 4 mM (Example 1); the upper graphs each show the fluorescent spectra with an ordinate axis of an RFU value (absolute value), the middle graphs each show the fluorescent spectra with an ordinate axis of an RFU value (relative value) and the lower graphs each show the absorption spectra.
Figure 8:
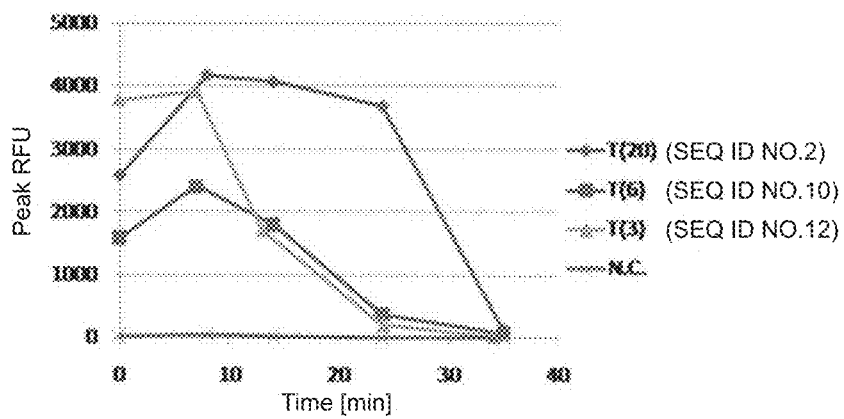
FIG. 8 Graphs each substituting a drawing and showing a change with elapsed time of fluorescent spectra and absorption spectra obtained in oligo-DNAs T(20), T(6) and T(3) under the condition of a $CuSO_4$ concentration of 0.4 mM and an S.A. concentration of 4 mM (Example 1); (A) shows a change with elapsed time of the peak RFU value, and (B) shows a change with elapsed time at a wavelength of 346 nm.
Figure 8:
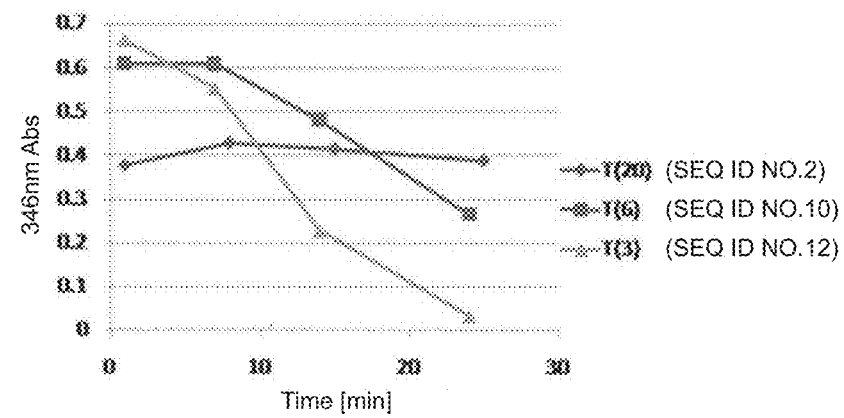

Next, a change with elapsed time of fluorescent spectra and absorption spectra obtained in oligo-DNAs T(20), T(6) and T(3) under the condition of a $CuSO_4$ concentration of 0.4 mM and an S.A. concentration of 4 mM. The S.A. was added directly before the measurements of the fluorescent spectrum and the absorption spectra for the first time. After 8, 14, 24 and 35 minutes, the fluorescent spectra and the absorption spectra were measured. The results are shown in FIGS. 7 and 8. In FIG. 7, the upper graphs each show the fluorescent spectrum with an axis of an RFU value (absolute value), the middle graphs each show the fluorescent spectrum with an ordinate axis of an RFU value (relative value) and the lower graphs each show the absorption spectrum. FIG. 8 shows a change with elapsed time of the peak RFU value (A), and shows a change with elapsed time at a wavelength of 346 nm (B).

As shown in the Figures, fluorescence is almost disappeared in all oligo-DNAs of (T20), T(6) and (T3) after 30 minutes. In particular, the fluorescence is quickly disappeared in the oligo-DNAs having short base lengths. After 35 minutes, the fluorescent spectra were measured. Immediately thereafter, 1.8 µl of 44 mM S.A. solution was again added to the sample for measurement. The fluorescence could be again detected. From this, the disappearance of the fluorescence could be considered due to oxidation of Cu(I) ions to Cu(II) ions. In each of the fluorescent spectra of the oligo-DNAs T(6) and T(3), as the peak intensity was decreased, a new peak was observed at a short wavelength side.

On the other hand, in each of the absorption spectra of the respective oligo-DNAs, a decrease in the peak intensity was observed with elapsed time. The absorption spectra were more gradually decreased as compared with the fluorescent spectra.

Figure 9:
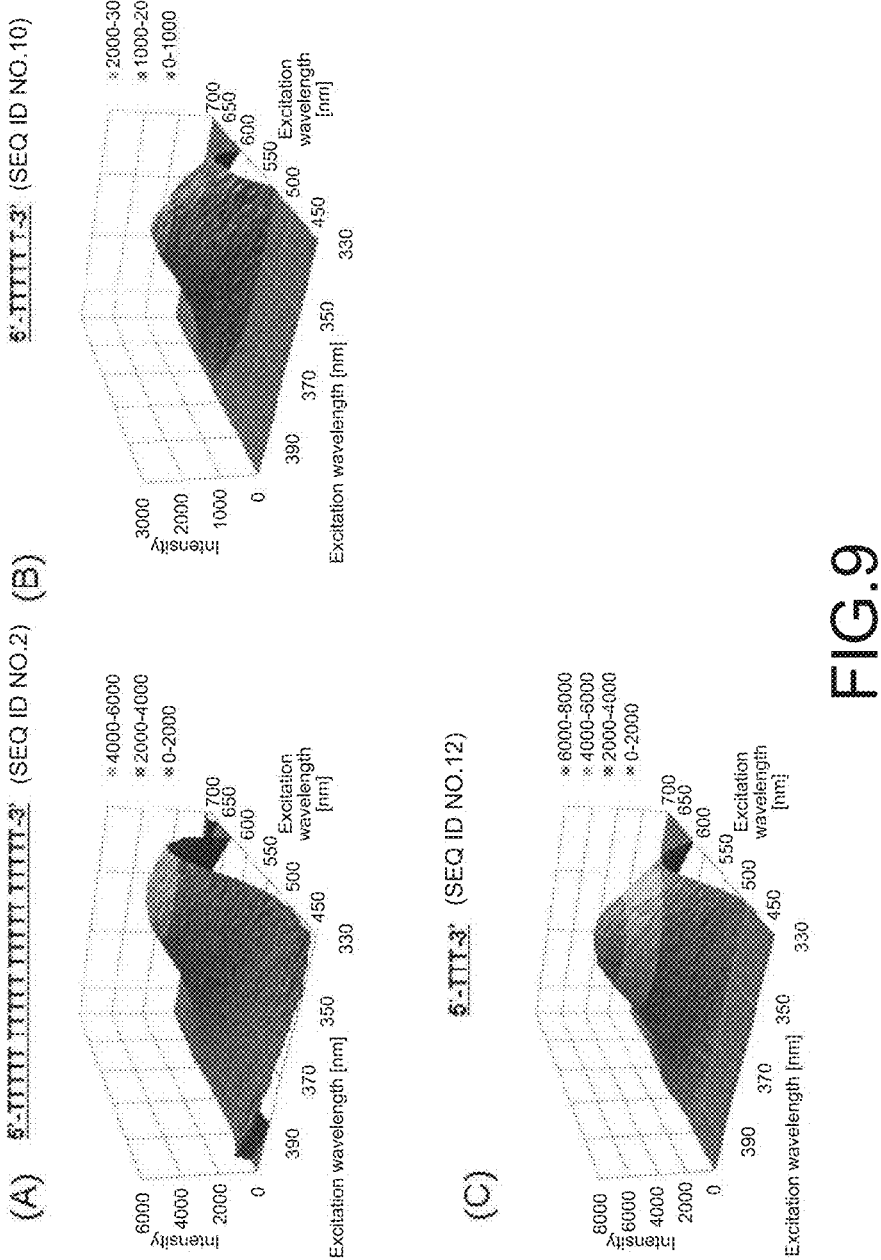
FIG. 9 Graphs each substituting a drawing and showing a two-dimensional fluorescent spectrum acquired in oligo-DNAs T(20), T(6) and T(3).
Figure 10:
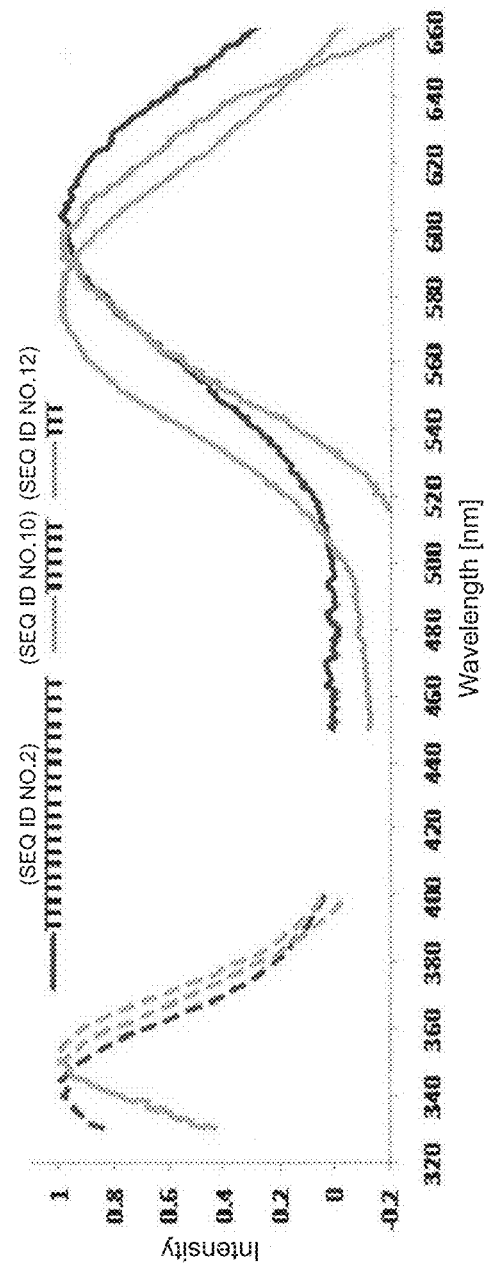
FIG. 10 A graph substituting a drawing and showing excitation spectra (broken lines) and fluorescent spectra (solid lines) obtained in oligo-DNAs T(20), T(6) and T(3) (Example 1).

FIG. 9 (A) to (C) show two-dimensional fluorescent spectra acquired in oligo-DNAs T(20), T(6) and T(3) by the type F-4500 spectrofluorophotometer. FIG. 10 shows excitation spectra (broken lines) and fluorescent spectra (solid lines) obtained in the respective oligo-DNAs. The spectrum was measured at a space of 1 nm for a fluorescent wavelength, and at a space of 2 nm for an excitation wavelength.

As shown in the Figures, it was confirmed that the patterns of the fluorescent spectra were changed depending on the base lengths of the oligo-DNAs. It was also confirmed that the patterns of the excitation spectra were changed depending on the base lengths.

Figure 11:
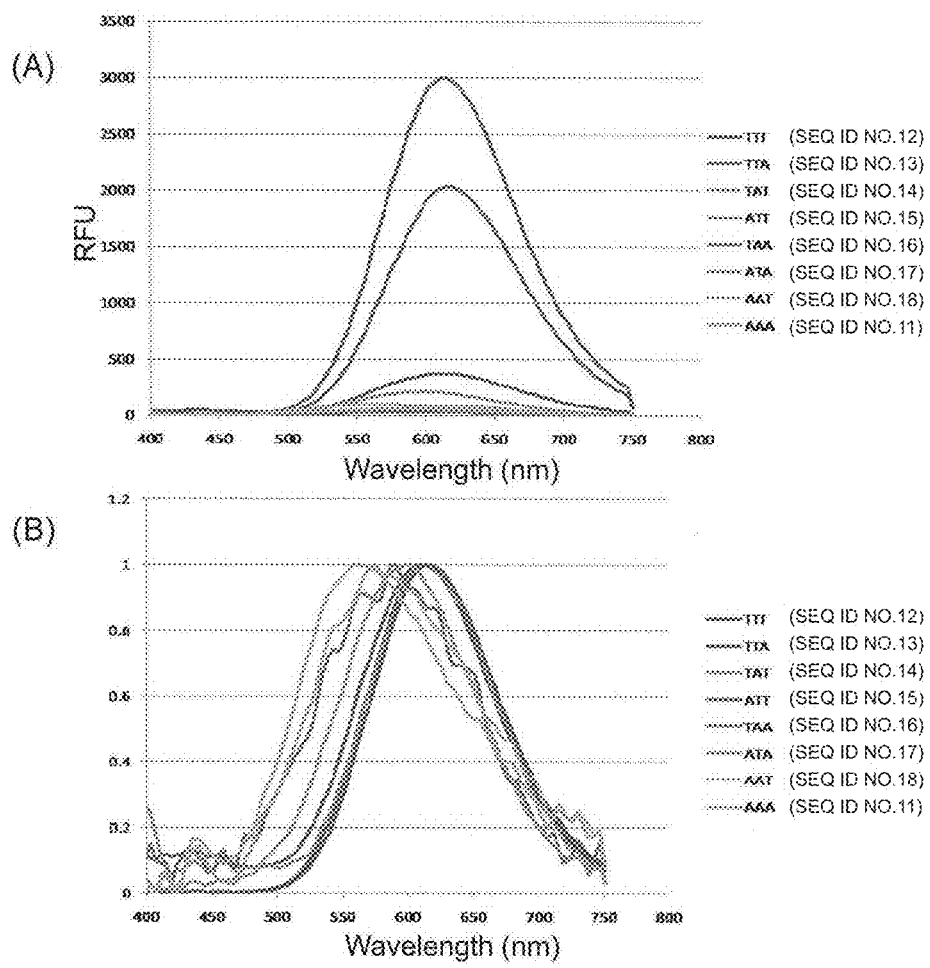
FIG. 11 Graphs each substituting a drawing and showing fluorescent spectra obtained in oligo-DNAs including a three base length sequence by combining adenine and thymine (Example 1).
Figure 12:
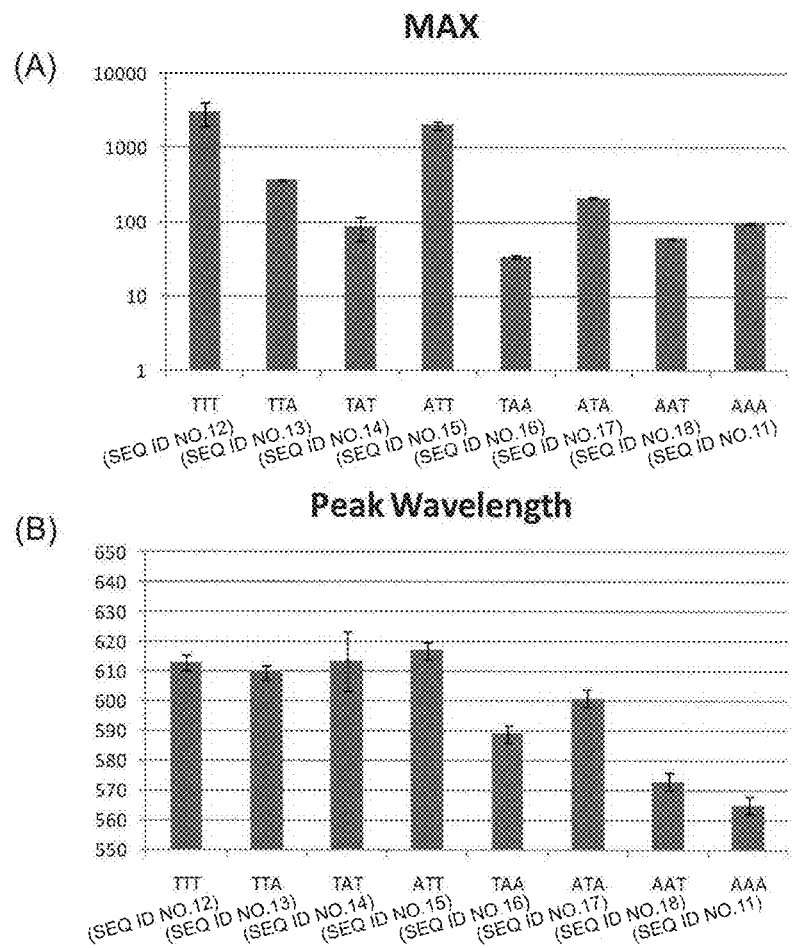
FIG. 12 Graphs each substituting a drawing and showing a maximum RFU value (A) and a peak FRU wavelength (B) of the fluorescent spectra obtained in oligo-DNAs including a three base length sequence by combining adenine and thymine (Example 1).

In order to further examine a relationship between the base sequences and the spectra, the oligo-DNAs each having a three base length sequence by a combination of adenine (A) and thymine (T) described in SEQ ID NOS. 11 and 18 were measured for the fluorescence. The results are shown in FIGS. 11 and 12. In FIG. 11, an ordinate axis (A) represents an RFU value in each wavelength measured by the Nanodrop and an ordinate axis (B) represents a value provided by dividing the RFU value in each wavelength by a maximum RFU value. FIG. 12 shows an average value and a standard error by measuring the maximum value of the RFU and the peak wavelength for three times.

As shown in the Figures, it was confirmed that the fluorescence intensity and the peak wavelength were changed depending on the base sequences of the oligo-DNAs.

Figure 13:
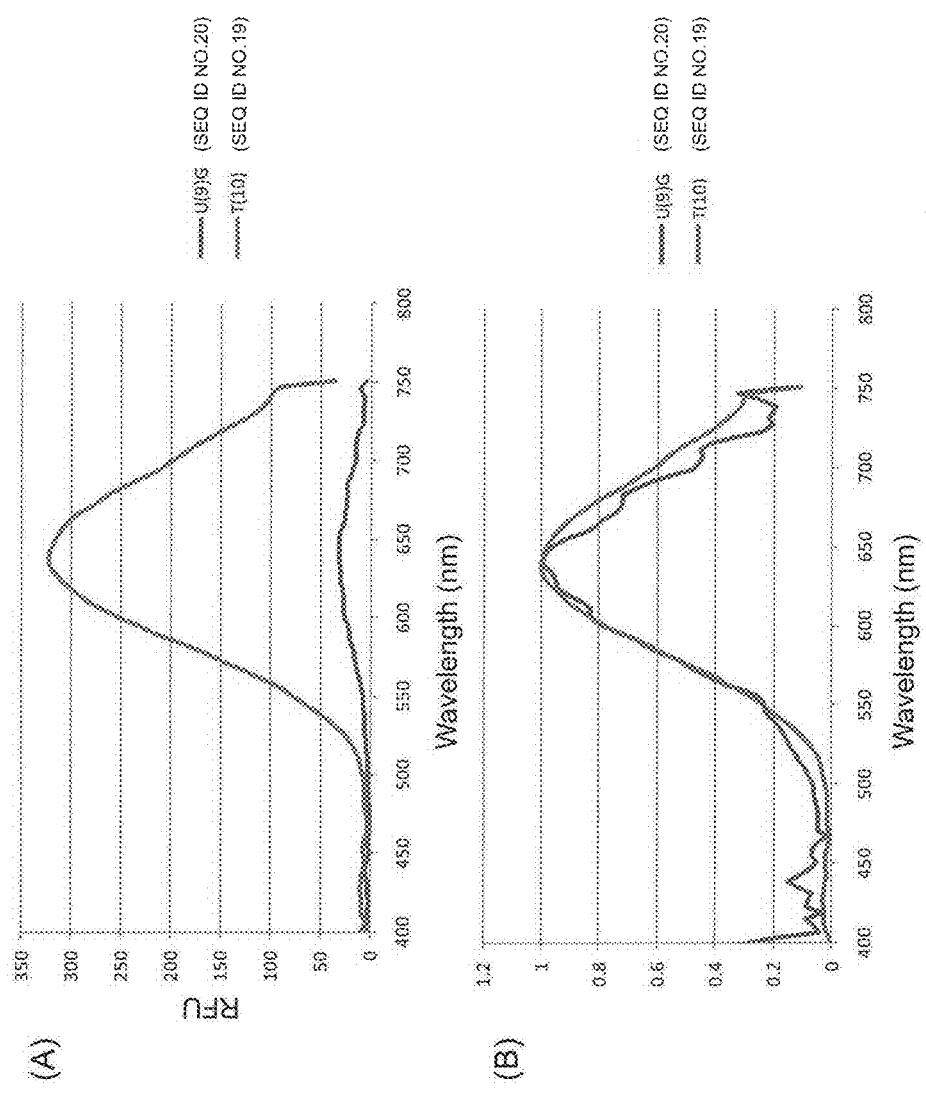
FIG. 13 Graphs each substituting a drawing and showing the fluorescent spectra obtained in oligo-DNAs including sequences of SEQ ID NOS. 19 and 20 (Example 1).

FIG. 13 shows the results of the measurement obtained in the oligo-DNAs including sequence of SEQ ID NOS. 19 and 20. It was confirmed that the oligo-DNAs having the sequence described in SEQ ID NO. 20 containing uracil (U) emitted the fluorescence having the spectrum shape and the peak position similar to that of the oligo-DNAs having the sequence described in SEQ ID NO. 19 containing thymine (T), although the fluorescence intensity in the oligo-DNAs having the sequence described in SEQ ID NO. 20 was faint as compared with those having the sequence described in SEQ ID NO. 19.

<Discussion>

This Example showed that the orange-colored fluorescence having a wavelength of about 500 nm to 700 nm was observed by ultraviolet irradiation when DNAs were mixed with a HEPPSO buffered solution containing sodium chloride into which $CuSO_4$ and the S.A. were mixed. It was confirmed that the fluorescence intensity depended on the concentration of $CuSO_4$, and the fluorescence intensity and the spectrum were also influenced by the base sequences of the nucleic acids.

The fluorescence was observed in the oligo-DNAs containing at least thymine (T), adenine (A) or uracil (U). In the experiment where the oligo-DNAs each having a three base length containing thymine (T) and adenine (A) were used, the fluorescence was observed in any sequence. In addition, it is shown that the fluorescence intensity and the spectra were influenced not only by the amount of thymine (T) or adenine (A), but also by the position (sequence order) on the oligo-DNAs.

With time elapsed after the addition of the S.A., the fluorescence intensity was decreased with time, but was recovered by re-addition of the S.A. In the meantime, Cu(I) ions are very unstable in the presence of oxygen, and are changed into Cu(II) or solid copper as soon as the reduction effect of the S.A. is lost. From this, it is considered that the fluorescence is derived from the composite of Cu(I) ions and the nucleic acids. In order to detect the fluorescence by the interaction between copper and the nucleic acids, it may be desirable that a contact of the reaction solution with oxygen in the air be minimized.

Example 2

Example 2 illustrates that orange-colored fluorescence similar to that observed in Example 1 was emitted by ultraviolet irradiation under certain conditions when a solution containing nucleic acids was contacted with solid copper.

<Material and Method>

As the copper that was contacted with the nucleic acids, copper powder (Copper, Powder, −75 um, 99.9%/Cat. No. 030-18352/manufactured by Wako Pure Chemical Industries, Ltd., Osaka, Japan) was used.

As the RNAs, Rat Brain Total RNAs (Cat. No. 636622, Takara Bio Inc., Otsu, Japan) were used by dissolving it to DEPC treated water (Cat. No. 312-90201/Wako Pure Chemical Industries, Ltd., Japan).

PIPES, ACES, BES, TAPSO, HEPPSO, EPPS, TAPS, CAPS, TES, Tricine and OPSO were purchased from DOJINDO Laboratories (Kumamoto, Japan). Each of these was used by adjusting the pH pursuant to the protocols provided by the manufacturer. Other reagents were the same as in Example 1.

The nucleic acids were contacted with copper by mixing a variety of nucleic acids, salts and copper powder into a total amount of 40 microliters solution, and agitating it for 15 minutes. The amount of the copper powder added was 375 mg per milliliter of the solution, unless otherwise noted. The amount of the salt, or sodium chloride (NaCl), was 500 mM, unless otherwise noted.

After the sample was centrifuged to settle the copper powder, a supernatant was measured for the spectrum of the fluorescence and the intensity. The measurement of the spectra of the fluorescence and the intensity was performed in the similar steps as in Example 1.

<Results>

Figure 14:
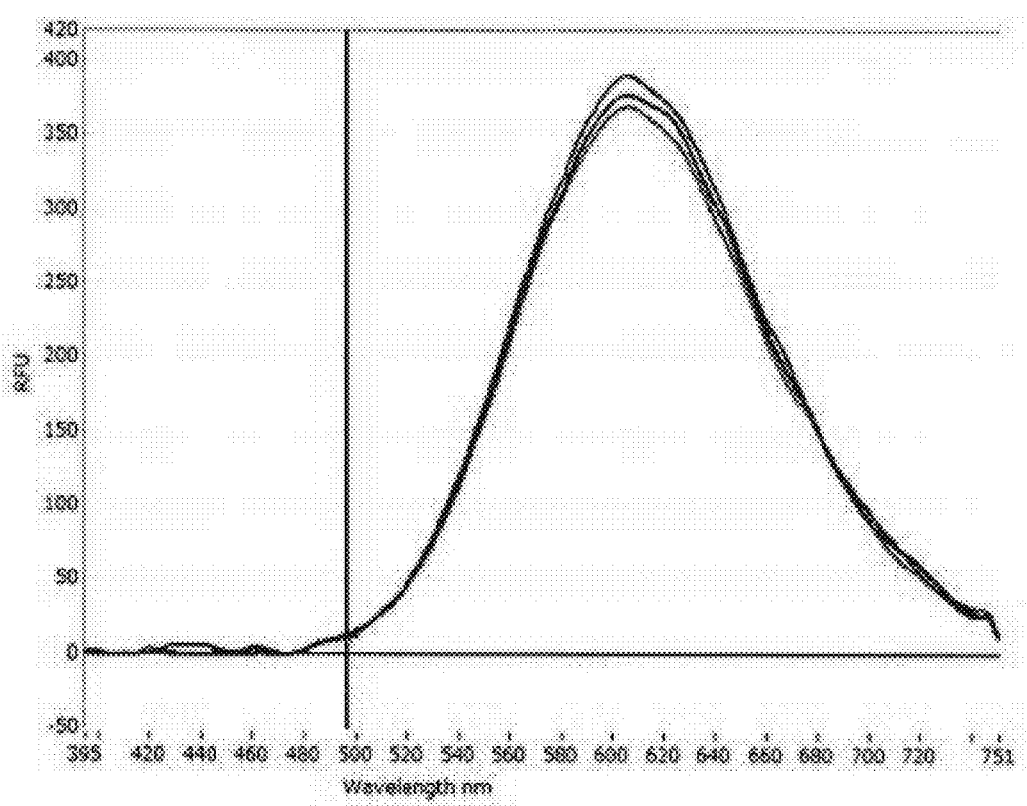
FIG. 14 A graph substituting a drawing and showing fluorescent spectra obtained by bringing a sample containing ssDNAs into contact with solid copper (Example 2).

The reaction solution to which 1.5 mg/ml of ssDNAs were added was measured for the fluorescence three times. The results are shown in FIG. 14 (abscissa axis: wavelength, ordinate axis: RFU). As shown in the Figure, when the sample containing the nucleic acids was contacted with solid copper and then UV-excited, the fluorescence having a peak around 600 nm could be detected.

Figure 15:
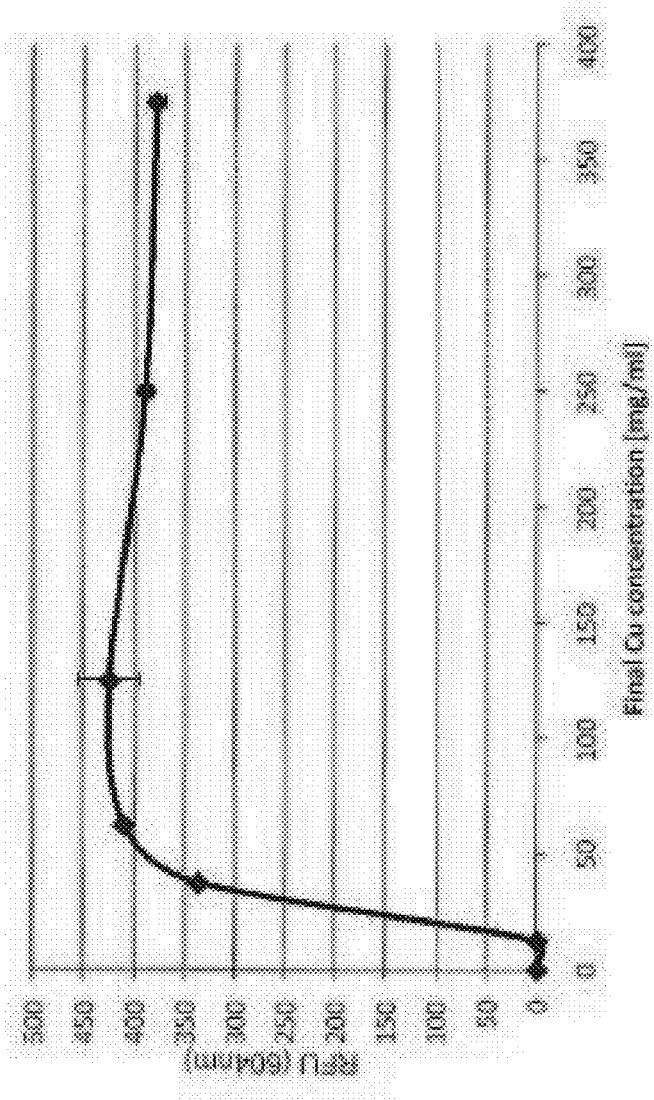
FIG. 15 A graph substituting a drawing and showing a fluorescent spectrum obtained by bringing a sample containing ssDNAs into contact with solid copper having different concentrations (Example 2).

Next, a reaction solution was prepared by adding the copper powder in the amount of 375 mg, 250 mg, 125 mg, 62.5 mg, 37.5 mg, 12.5 mg and 0 mg based on 1 mL of the reaction solution. To the reaction solution, 1.5 mg/ml of ssDNAs were added. The fluorescence was measured for three times. The result was shown in FIG. 15. As shown in the Figure, the fluorescence intensity depended on the amount of the copper powder. In the Cu powder used in this Example, apparent fluorescence was observed when the amount was 37.5 mg/ml or more. On the other hand, no apparent fluorescence was observed when the amount was 12.5 mg/ml or less.

Figure 16:
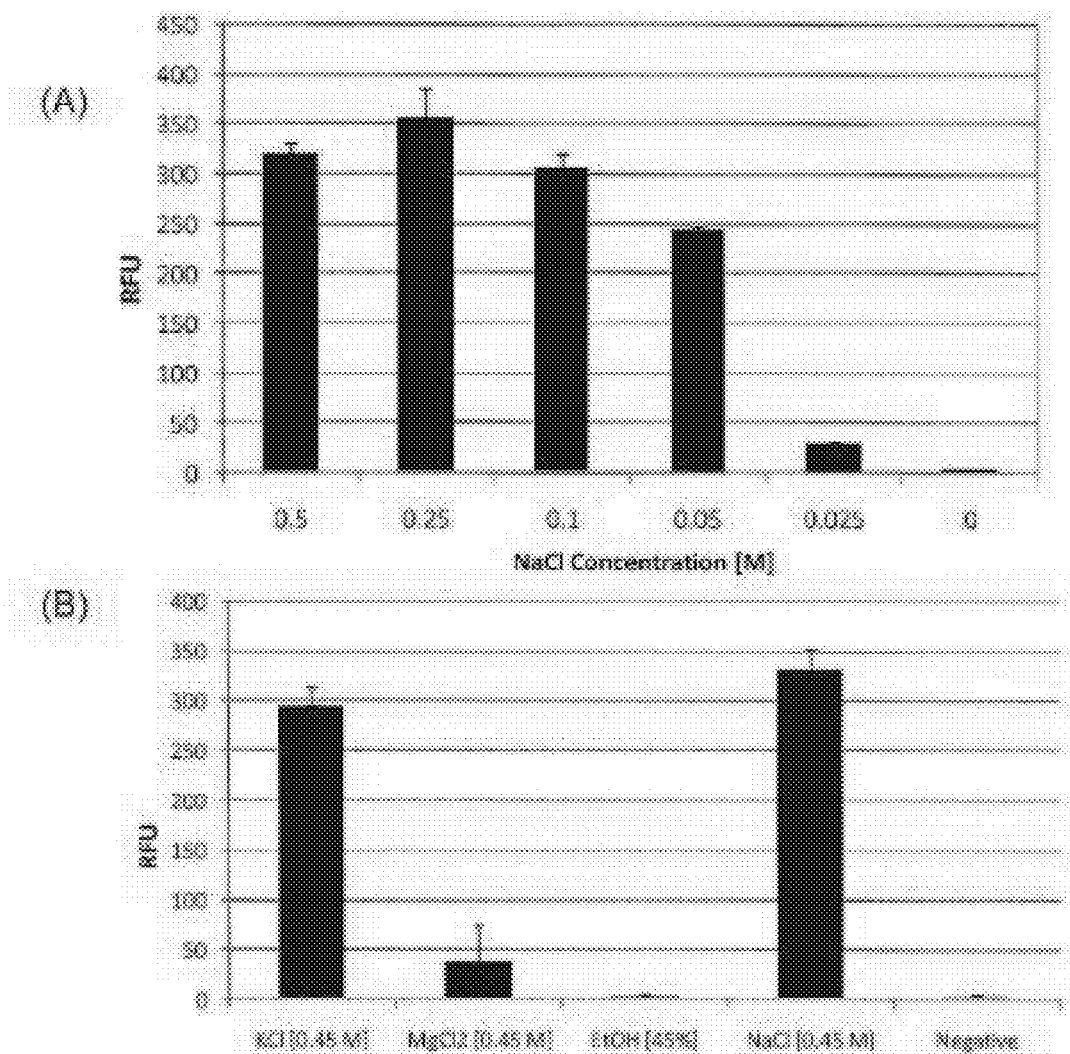
FIG. 16 Graphs each substituting a drawing and showing fluorescent spectra obtained by bringing a sample containing ssDNAs into contact with a reaction solution containing a salt having different types or concentrations (Example 2).

Then, the type and the concentration of the salt in the reaction solution were changed. To the reaction solution, 1.5 mg/ml of ssDNAs were added. The intensities of the fluorescence detected were compared. The results are shown in FIG. 16. (A) shows the fluorescence intensity detected in the reaction solution to which 0.5, 0.25, 0.1, 0.05, 0.025 and 0 M sodium chloride (NaCl) were added. (B) shows the fluorescence intensity detected in the reaction solution to which 0.45 M sodium chloride (NaCl), 0.45 M potassium chloride (KCl), 0.45 M magnesium chloride (MgCl2) and 45% ethanol (EtOH) were added. The fluorescence intensity was represented by the RFU at 604 nm, and measured for three times. The result was shown as the average and the standard error. As shown in the Figure, the fluorescence intensity depended on the amount of sodium chloride. Also, the fluorescence was detected under the coexistence of potassium chloride and magnesium chloride as well as sodium chloride.

Figure 17:
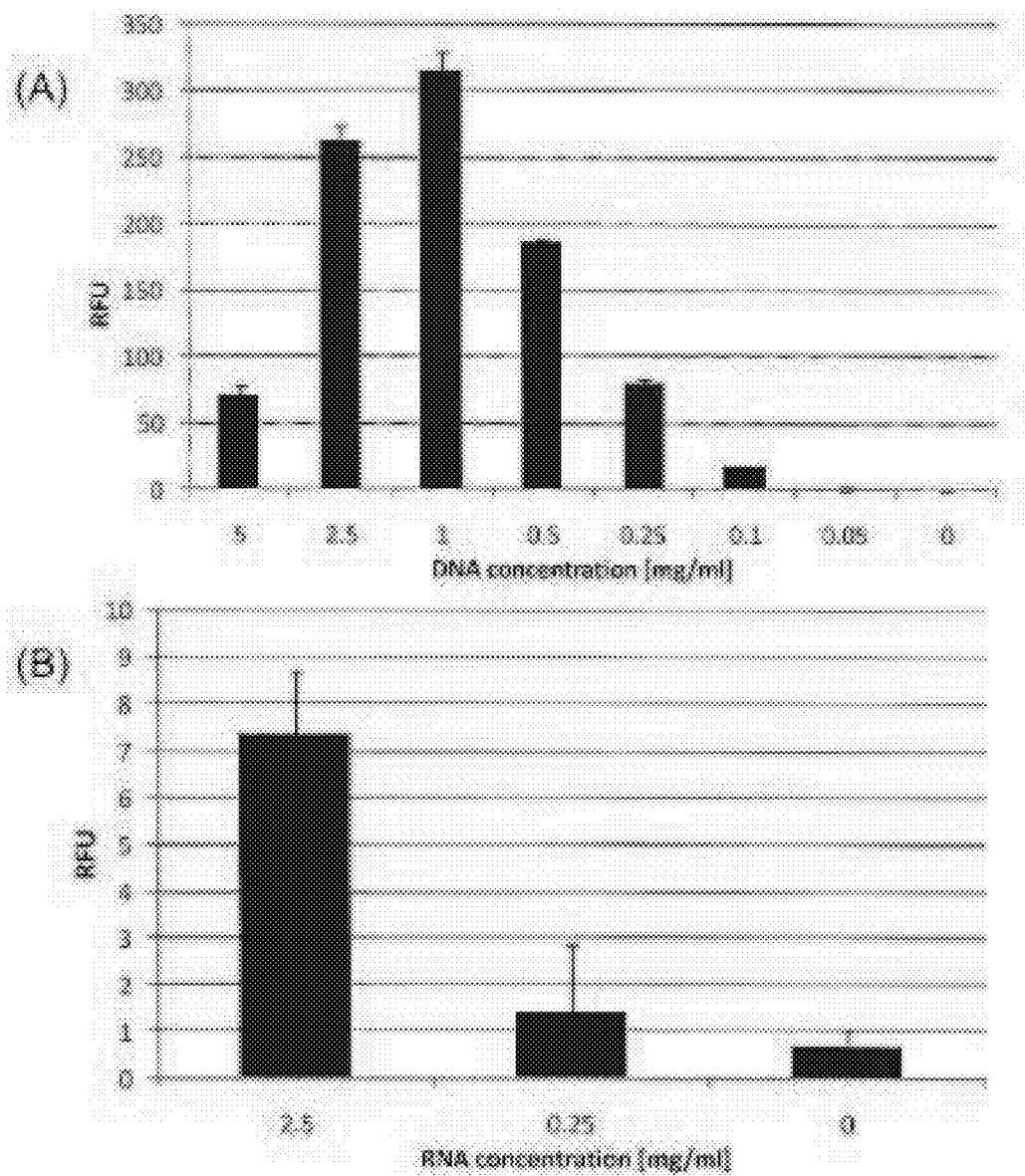
FIG. 17 Graphs each substituting a drawing and showing fluorescent spectra obtained by bringing a sample containing ssDNAs (A) or RNAs (B) having different concentrations with into contact solid copper (Example 2).

FIG. 17 shows comparison results of the fluorescence intensity detected when the concentration of the nucleic acids added to the reaction solution was changed. (A) shows the fluorescence intensity detected in the reaction solution to which 5, 2.5, 1, 0.5, 0.25, 0.1, 0.05, and 0 mg/ml of ssDNAs were added. (B) shows the fluorescence intensity detected in the reaction solution to which 2.5, 0.25, and 0 mg/ml of RNAs were added. The abscissa axis represents the concentration of the nucleic acids, and the ordinate axis represents the RFU at a fluorescent wavelength of 604 nm. The measurement was performed for three times. The concentration of sodium chloride (NaCl) was 0.25M, and the amount of the copper power was 200 mg per 1 ml. The condition was used in the following experiments, unless otherwise noted. As shown in the Figure, the fluorescence intensity depended on the concentration of DNAs and the concentration of RNAs.

Figure 18:
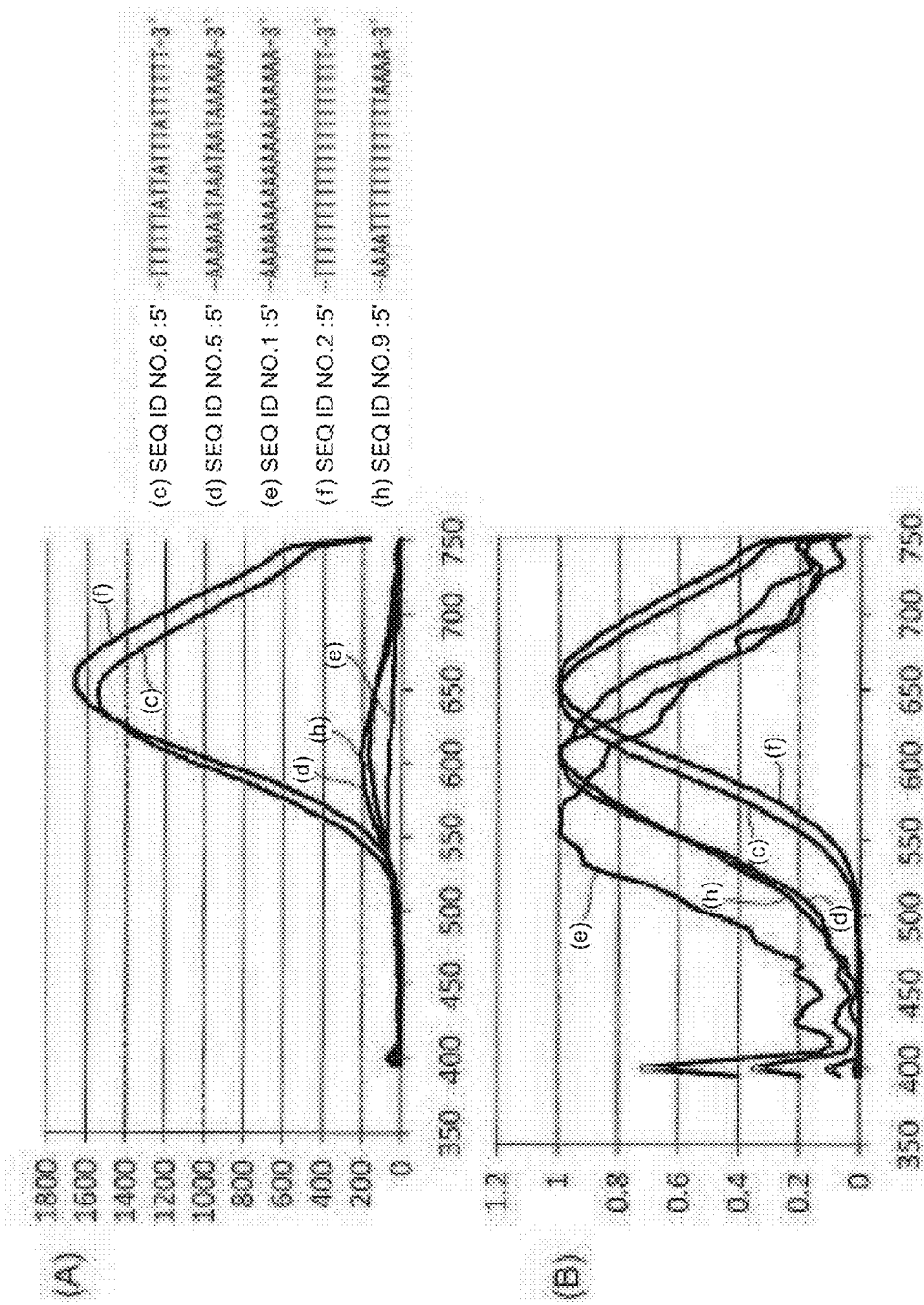
FIG. 18 Graphs each substituting a drawing and showing fluorescent spectra obtained by bringing a sample containing oligo-DNAs having different sequences into contact with solid copper (Example 2).

Next, the reaction solution to which 0.1 mM oligo-DNAs having different sequences described in SEQ ID NOS. 1, 2, 5, 6 and 9 was measured for the fluorescence. The results are shown in FIG. 18. An ordinate axis (A) represents an RFU value measured by the Nanodrop, and an ordinate axis (B) represents a relative RFU value when the peak height was set to 1. As shown in the Figure, the fluorescence intensity and the peak wavelength were influenced by the base sequences. In particular, it could be confirmed that when the percentage of thymine (T) was high, the fluorescence intensity was high and the peak wavelength became longer.

Figure 19:
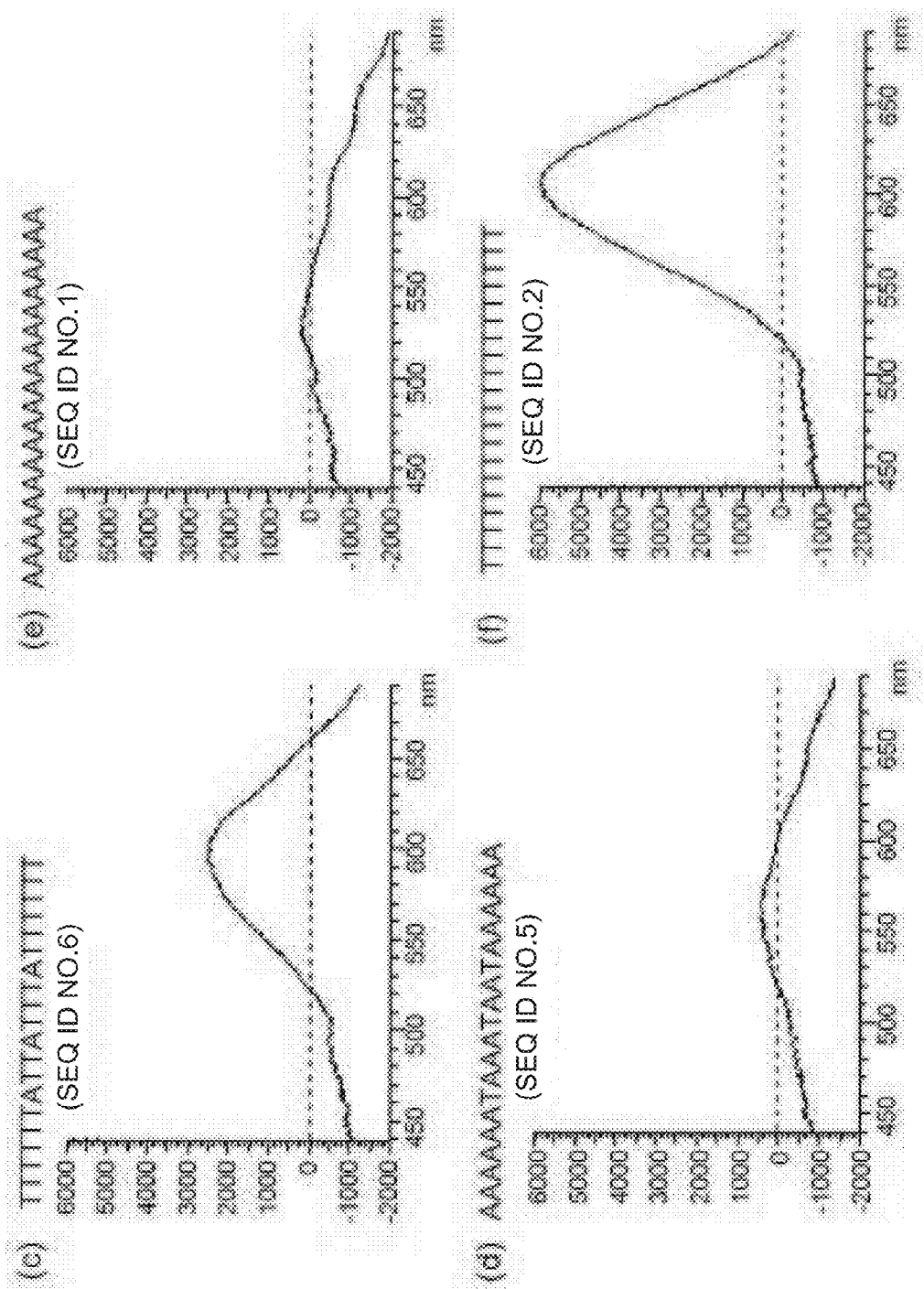
FIG. 19 Graphs each substituting a drawing and showing a fluorescent spectrum obtained by bringing a sample containing oligo-DNAs having different sequences into contact with solid copper (Example 2).
Figure 20:
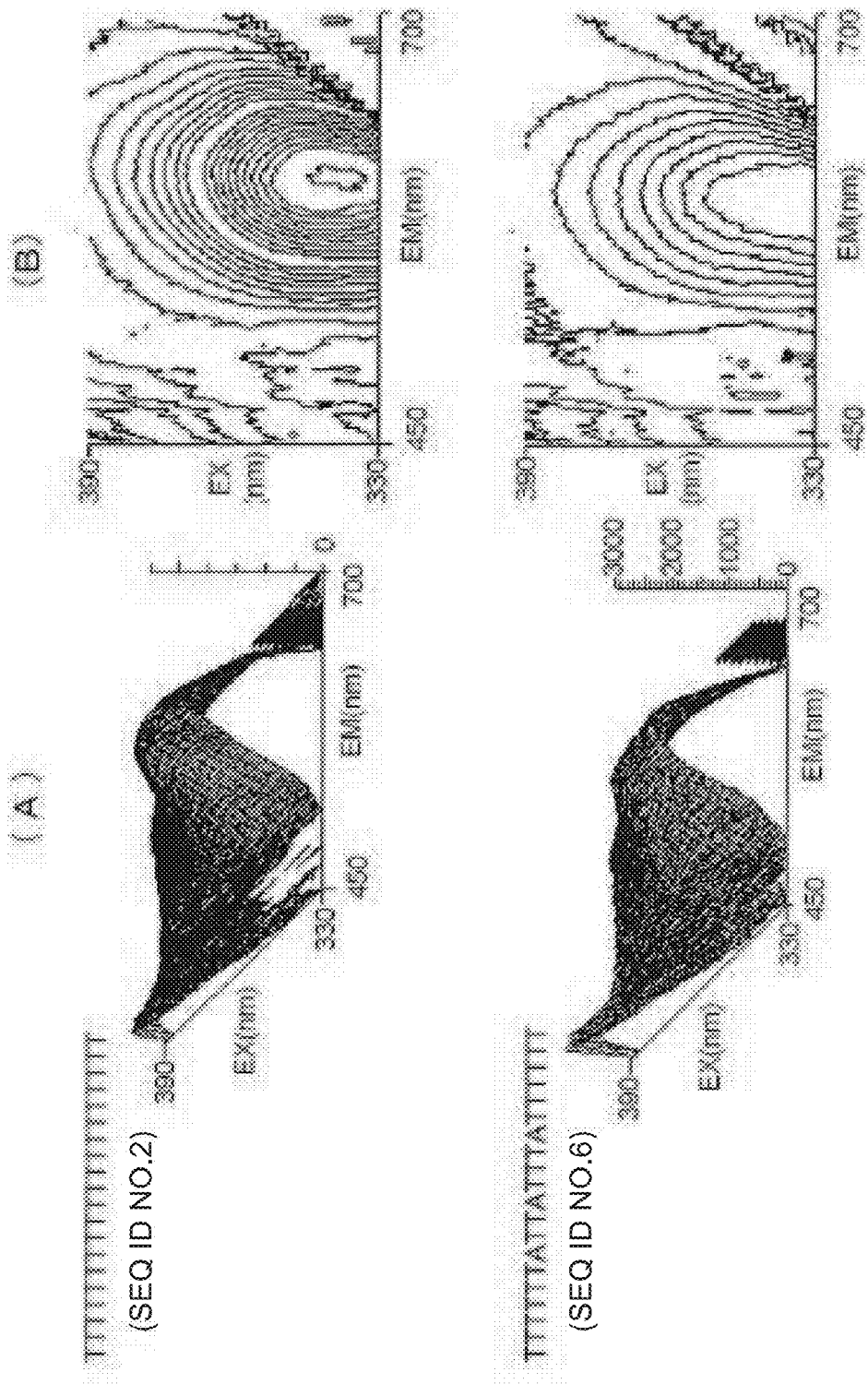
FIG. 20 Graphs each substituting a drawing and showing excitation-fluorescent spectra obtained by bringing a sample containing oligo-DNAs having different sequences into contact with solid copper (Example 2).

The reaction solution to which oligo-DNAs having sequences described in SEQ ID NOS. 1, 2, 5 and 6 was also measured using the type F-4500 spectrofluorophotometer. FIG. 19 shows the results of the fluorescent spectra (slit width of 2.5 nm) within 400 nm to 700 nm when the excitation light of 360 nm (slit width of 10 nm) was irradiated. Again, it could be confirmed that when the percentage of thymine (T) was high, the fluorescence intensity was high and the peak wavelength became longer in the sequence containing thymine (T) and adenine (A). FIG. 20 shows the results by scanning the excitation light at 330 nm to 390 nm (slit width of 3 nm) and 400 nm to 700 nm (slit width of 2.5 nm) to measure excitation–fluorescent spectra. (A) represents three dimensionally, and (B) represents a contour. An axis EX represents an excitation wavelength (nm), an axis EM represents a fluorescence wavelength (nm) and a height direction represents the fluorescence intensity. Based on the results, it could be read that the excitation, the fluorescent spectra and the intensity were changed by the different base sequences of the DNAs.

Figure 21:
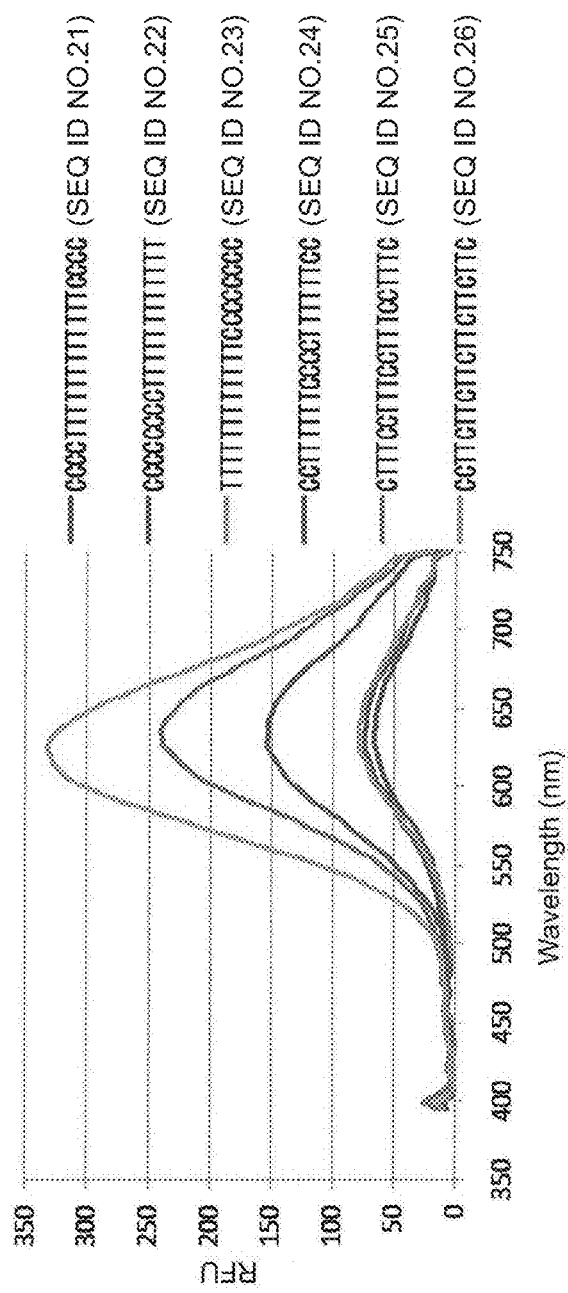
FIG. 21 A graph substituting a drawing and showing fluorescent spectra obtained in oligo-DNAs having combination sequences of eight-base cytosine and 12-base thymine (Example 2).

In order to further examine a relationship between the base sequences and the spectrum, the oligo-DNAs each having a combination sequence of cytosine (C) having eight bases and thymine (T) having 12 bases described in SEQ ID NOS. 21 and 26 were measured for the fluorescence. The results are shown in FIG. 21. As shown in the Figure, the fluorescence intensity differed when the sequence was different even if the base composition of the DNAs was the same.

Figure 22:
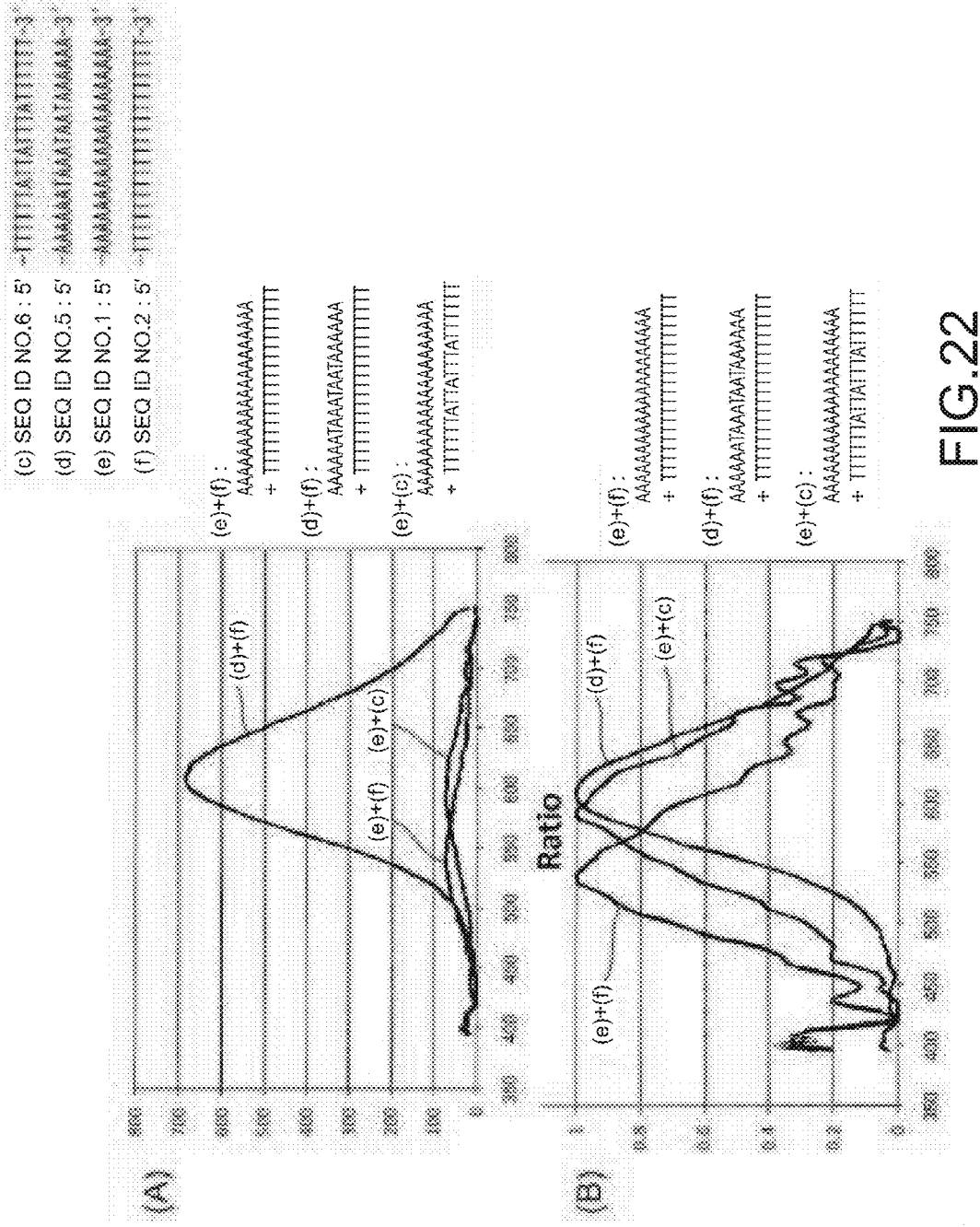
FIG. 22 Graphs each substituting a drawing and showing fluorescent spectra obtained in double-stranded DNAs including a mismatch (Example 2).

Next, the double-stranded DNAs including a mismatch were measured for the pattern of the fluorescent spectrum. As the double-stranded DNAs, three types: a mixture ((e)+(f)) of oligo-DNAs each having a sequence shown in SEQ ID NO. 1 and oligo-DNAs each having a sequence shown in SEQ ID NO. 2, a mixture ((d)+(f)) of oligo-DNAs each having a sequence shown in SEQ ID NO. 5 and oligo-DNAs each having a sequence shown in SEQ ID NO. 2, and a mixture ((e)+(c)) of oligo-DNAs each having a sequence shown in SEQ ID NO. 1 and oligo-DNAs each having a sequence shown in SEQ ID NO. 6 were used. Any of the oligo DNAs were mixed at a final concentration of 0.5 mg/ml. The results are shown in FIG. 22. An ordinate axis (A) represents an RFU value measured by the Nanodrop, and an ordinate axis (B) represents a relative RFU value when the peak height was set to 1. An abscissa axis represents a wavelength (nm). As shown in the Figure, the fluorescence intensity in the double-stranded DNAs was lower than that in the single-stranded DNAs. However, in the double-stranded DNAs having a mismatch of thymine (T), the strong fluorescence was confirmed.

Figure 23:
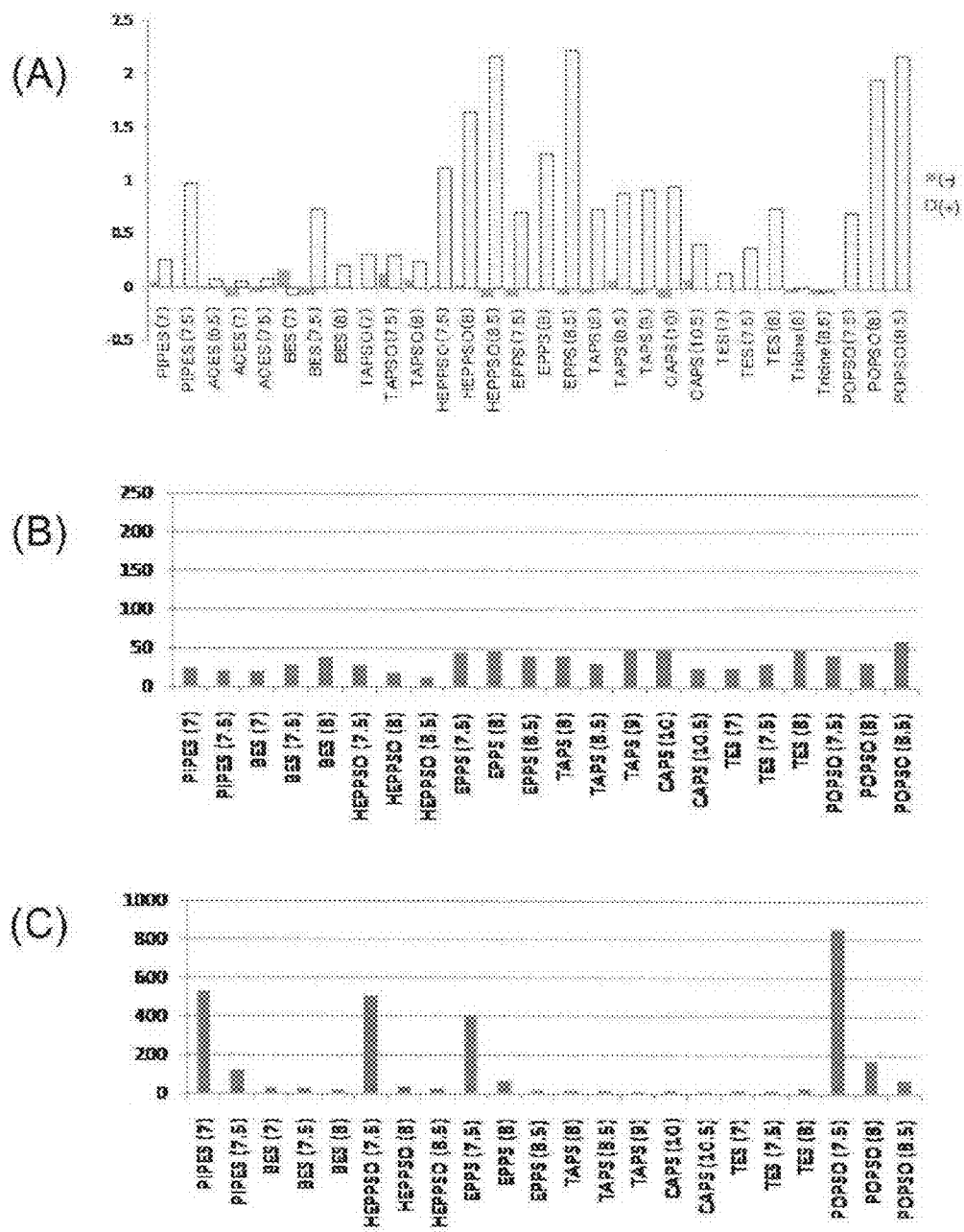
FIG. 23 Graphs each substituting a drawing and showing RFU values obtained by changing a type and a pH of a buffer of a reaction solution (Example 2).

The intensities of the fluorescence detected were compared, when the types of the buffer and the pH in the reaction solution were changed. The results are shown in FIG. 23. (A) shows relative values of peak RFU values of a sample (+) containing ssDNAs and a sample (−) containing no nucleic acids under each buffered condition. (B) shows a relative value of a peak RFU value of a sample containing oligo-DNAs having the sequence shown in SEQ. ID NO. 1 under the same condition. (C) shows a relative value of a peak RFU value of a sample containing oligo-DNAs having the sequence shown in SEQ. ID NO. 2 under the same condition. The concentration of each buffer was 50 mM, the final concentration of the ssDNAs was 0.5 mg/ml, and the final concentration of the oligo-DNAs was 25 mM. The relative value of the peak RFU value means that the peak RFU value measured under no buffered condition is set to 1. The fluorescence intensity depended on the types of the buffer. The fluorescence was almost not detected when no nucleic acids exist in the buffer.

<Discussion>

Based on the results in this Example, it revealed that the fluorescence could be detected under adequate conditions including the salt concentration, when the nucleic acids were contacted with solid copper powder, as is the case that the nucleic acids were contacted with Cu(I) ions. It seemed that the fluorescence observed in each case of copper ions and solid copper was provided by the same mechanism, because their properties such as wavelength properties and sequence dependency are almost the same. Also, the fluorescence was observed when the RNAs were used as the nucleic acids. In addition, in the double-stranded DNAs, strong fluorescence was observed when the mismatch exists especially in thymine (T). This suggested that binding with the complementary sequence might inhibit the formation of the fluorescent substance by binding the nucleic acids with copper. Also, it is considered that the increase in the fluorescence intensity at the mismatch site could be applied to a method of detecting for mutation in the base sequences of the nucleic acids.

In the experiments for comparing the fluorescence under each buffered condition, the fluorescence was observed in the buffer of PIPES, BES, HEPPSO, EPPS, TAPS, CAPS, TES and POPSO. In particular, strong fluorescence was detected in the buffer of PIPES, HEPPSO, EPPS and POPSO. The fluorescence could be observed within a pH range of 7.0 to 10.5. It was found that a change in the fluorescence intensity depending on the type of the buffer and the pH showed a different pattern depending on the base sequences of the nucleic acids. On the other hand, the buffer having a property to chelate and stabilize Cu(II) ions has a tendency that the fluorescence is not observed. Although no data is provided in this Example, the fluorescence was almost not observed when the reaction solution containing, for example, a tris buffer, EDTA or the like was used.

Example 3

In Example 3, it was confirmed that the fluorescence could be detected after the nucleic acids were brought into contact with copper sputtered on the surface of the glass, and the properties of the fluorescence were analyzed.

<Material and Method>

As the DNAs, the ssDNAs described in Example 1 were used. As the RNAs, the RNAs described in Example 2 were used.

Copper was sputtered on the surface of the glass using an apparatus, SH-350 manufactured by ULVAC, Inc. (Kanagawa, Tokyo) on which a Cu target, 99.99% (Kojundo Chemical Laboratory Co., Ltd, Saitama, Japan) was mounted. In the sputtering, a thickness was set to 40 nm, and an adequate sputtering time was set based on a deposition speed measured in advance. The glass for sputtering silver was manufactured by Kyodo International, Inc., Kanagawa, Japan.

On a slide glass on which copper or silver was sputtered or an untreated slide glass, a sample solution was placed, and a Gap cover glass, 24×25 NO. 4/#CG00024/Matsunami Glass Ind., Ltd., Osaka, Japan was covered thereon. After it was allowed to be stood for about 5 minutes, the fluorescence was observed. For the observation, an inverted microscope Ti-U (Nikon Co., Tokyo, Japan) was used. For capturing the fluorescence, a filter set UV-1A (Ex: 365/10, DM: 400, BA: 400/Nikon) was used. For capturing and recording an image, a digital CCD camera Retiga 2000R (QImaging, BC, Canada) and a ×20 objective lens were used.

<Results>

Figure 24:
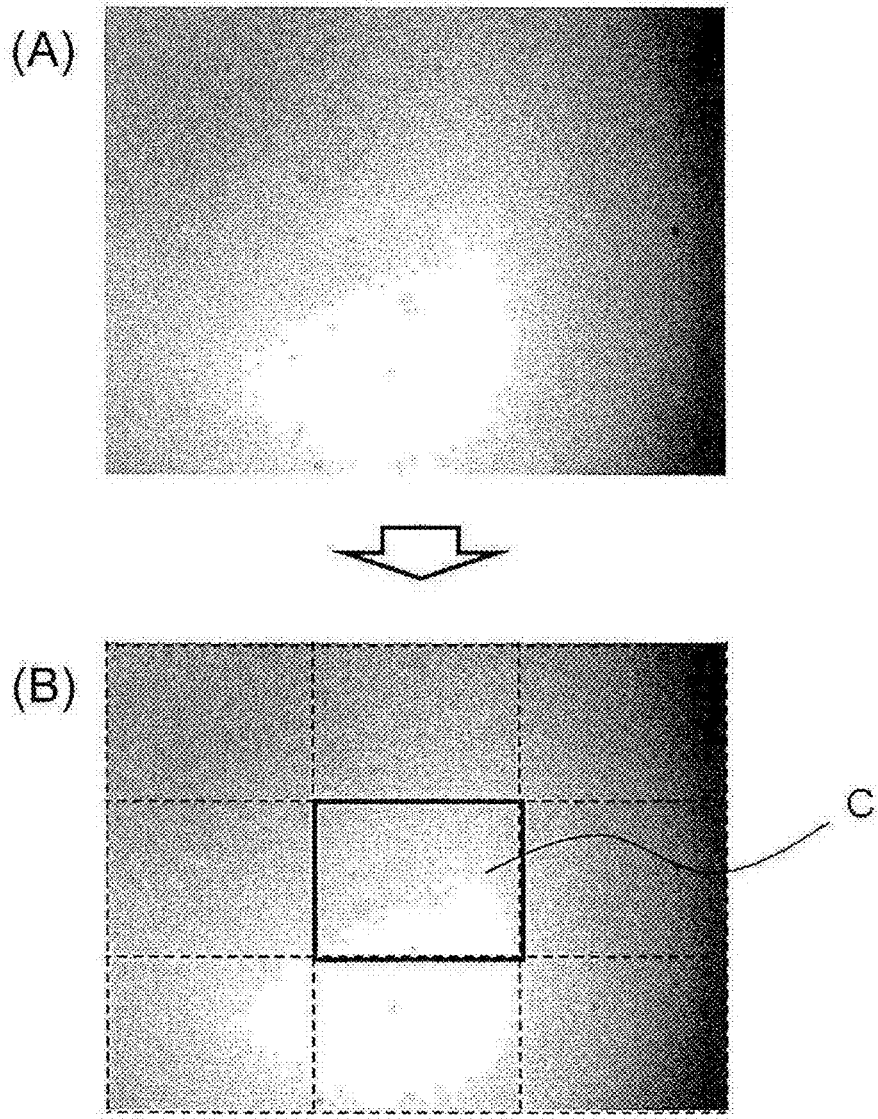
FIG. 24 Photographs each substituting a drawing and showing a fluorescent image obtained by bringing copper sputtered on a glass surface into contact with ssDNAs (Example 3).
Figure 25:
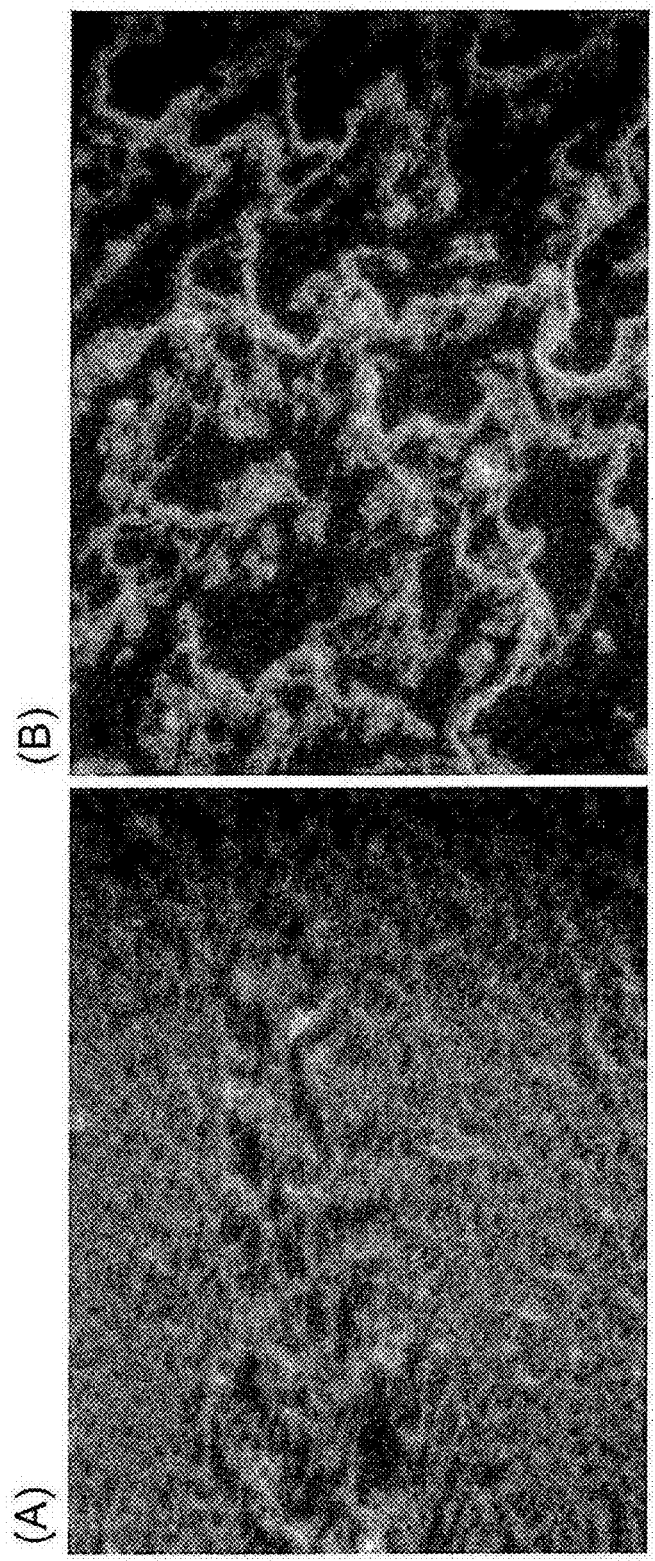
FIG. 25 Photographs each substituting a drawing and showing a fluorescent image obtained by bringing copper sputtered on a glass surface into contact with RNAs (Example 3).

FIG. 24 shows images captured after the sample containing 5 mg/ml of DNAs and 0.5 M of NaCl was allowed to stand for 5 minutes on the copper sputtered glass. FIG. 25 shows images captured after the sample containing 5 mg/ml of RNAs and 0.5 M of NaCl was allowed to stand for 5 minutes on the copper sputtered glass.

As shown in FIG. 24(A), when the sample containing DNAs was used, smooth fluorescence was observed on the entire captured image. On the other hand, as shown in FIGS. 25 (A) and (B), when the sample containing RNAs was used, the fluorescence having a specific wave-like pattern within the captured image was observed. A prospective cause of the pattern specific to the RNAs was that the single-stranded RNAs were hybridized each other to form the higher order structure.

Next, the fluorescence intensity within the captured image was converted into numerals. Each captured image was divided into nine sections as shown in FIG. 24 (B). One of the nine sections (symbol C in the Figure) was set to be a measuring range. An average value of the fluorescence intensity within the measuring range was calculated. For each sample, five parts on the slide were captured to calculate the average value from each image. The resultant five average values were further averaged and calculated for standard deviation.

Figure 26:
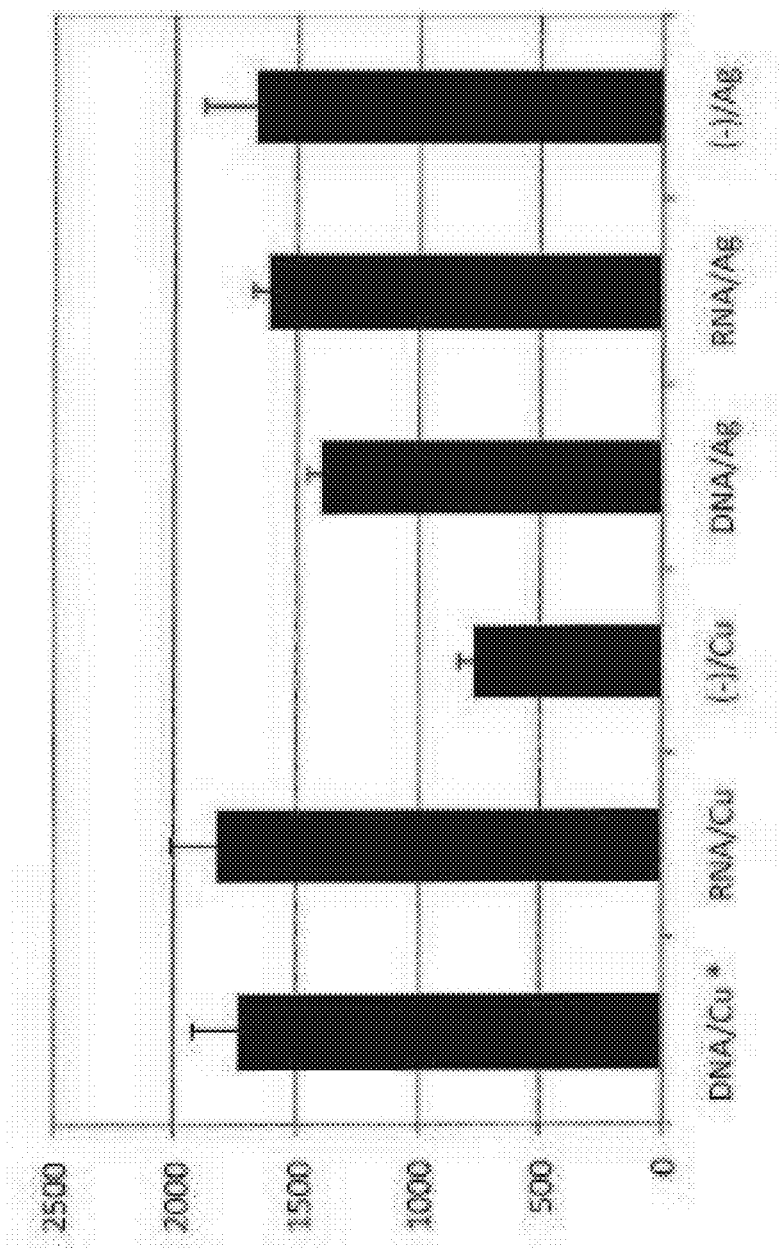
FIG. 26 A graph substituting a drawing and showing a fluorescence intensity obtained by bringing copper or silver sputtered on a glass surface into contact with a sample including DNAs or RNAs (Example 3).

FIG. 26 shows the fluorescence intensity acquired when the sample containing the DNAs or the RNAs was contacted with copper or silver sputtered on the glass. In FIG. 26, "DNA/Cu", "RNA/Cu", and "(−)/Cu" denote the sample containing 5 mg/ml DNAs, the sample containing 5 mg/ml of RNAs, and the sample containing no nucleic acids; the fluorescence intensity being measured on the Cu sputtered glass. In addition, "DNA/Ag", "RNA/Ag", and "(−)/Ag" denote the sample containing 5 mg/ml of DNAs, the sample containing 5 mg/ml of RNAs, and the sample containing no nucleic acids; the fluorescence intensity being measured on the Ag sputtered glass. Each sample contained 0.5 M NaCl. Since the fluorescence intensity in the "DNA/Cu" was significantly greater than those of the other samples, its exposure time was 1 minute. In all samples excluding the "DNA/Cu", the exposure time was 5 seconds.

As shown in the Figure, in the Cu sputtered glass, the "DNA/Cu" and the "RNA/Cu" had the fluorescence intensity higher than the "(−)/Cu". Especially in the DNA sample, the strong fluorescence was detected. On the other hand, in the Ag sputtered glass, the "DNA/Ag" and the "RNA/Ag" showed no increase in the fluorescence intensity as compared with the "(−)/Ag". As compared with the "(−)/Cu", the (−)/Ag" showed the higher measured value. This may be caused by a background derived from a reflected light, a scattered light or autofluorescence on the Ag sputtered surface.

Figure 27:
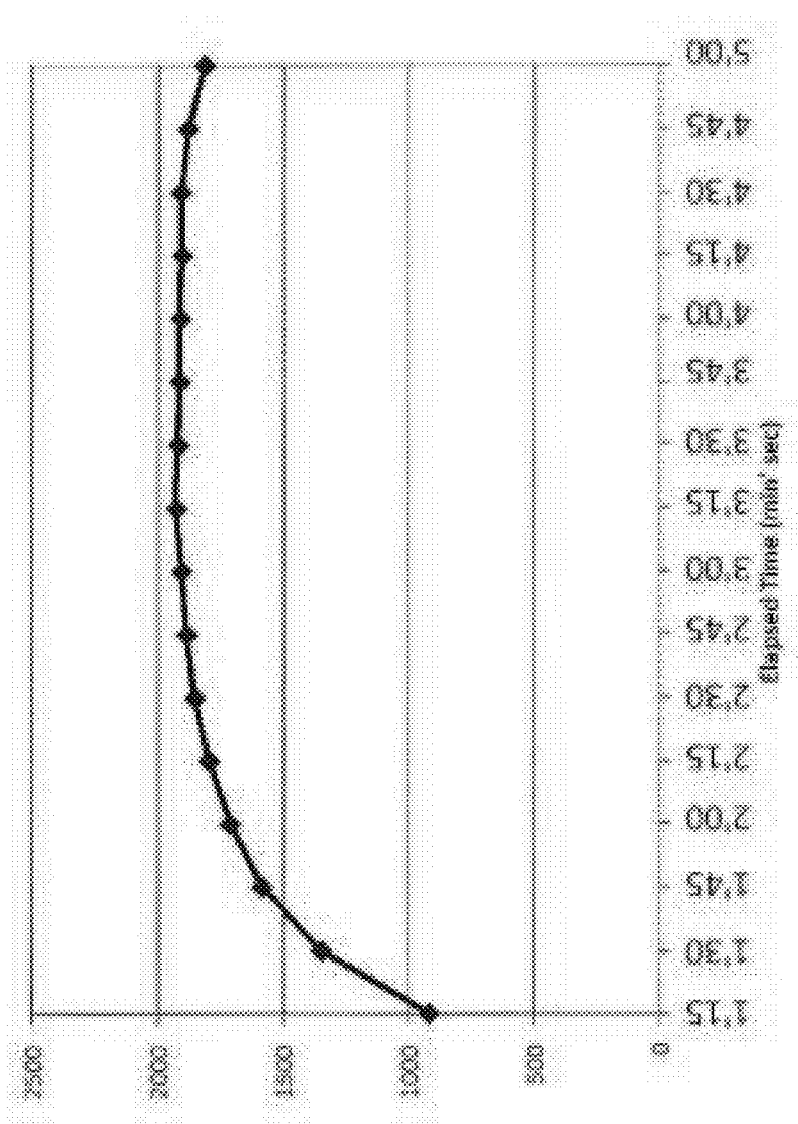
FIG. 27 A graph substituting a drawing and showing a change with elapsed time in a fluorescence intensity obtained by bringing copper sputtered on a glass surface into contact with ssDNAs (Example 3).

Next, a change in the fluorescence intensity with elapsed contact time of the nucleic acids with copper was examined. A point of time when the sample containing 5 mg/ml of ssDNAs and 0.5 M of NaCl was placed between the Cu sputtered glass and the Gap cover glass was designated as a starting point to measure the fluorescence intensity per predetermined time. The image was captured every 15 seconds, and a shutter for excitation light was opened and closed per capturing session. The 10× objective lens was used, and the exposure time was 1 second. In every time, one image captured was used to measure the fluorescence intensity. The results are shown in FIG. 27.

As shown in the Figure, the fluorescence intensity was gradually increased for several minutes after the sample was introduced, and reached the maximum value within about three minutes.

Figure 28:
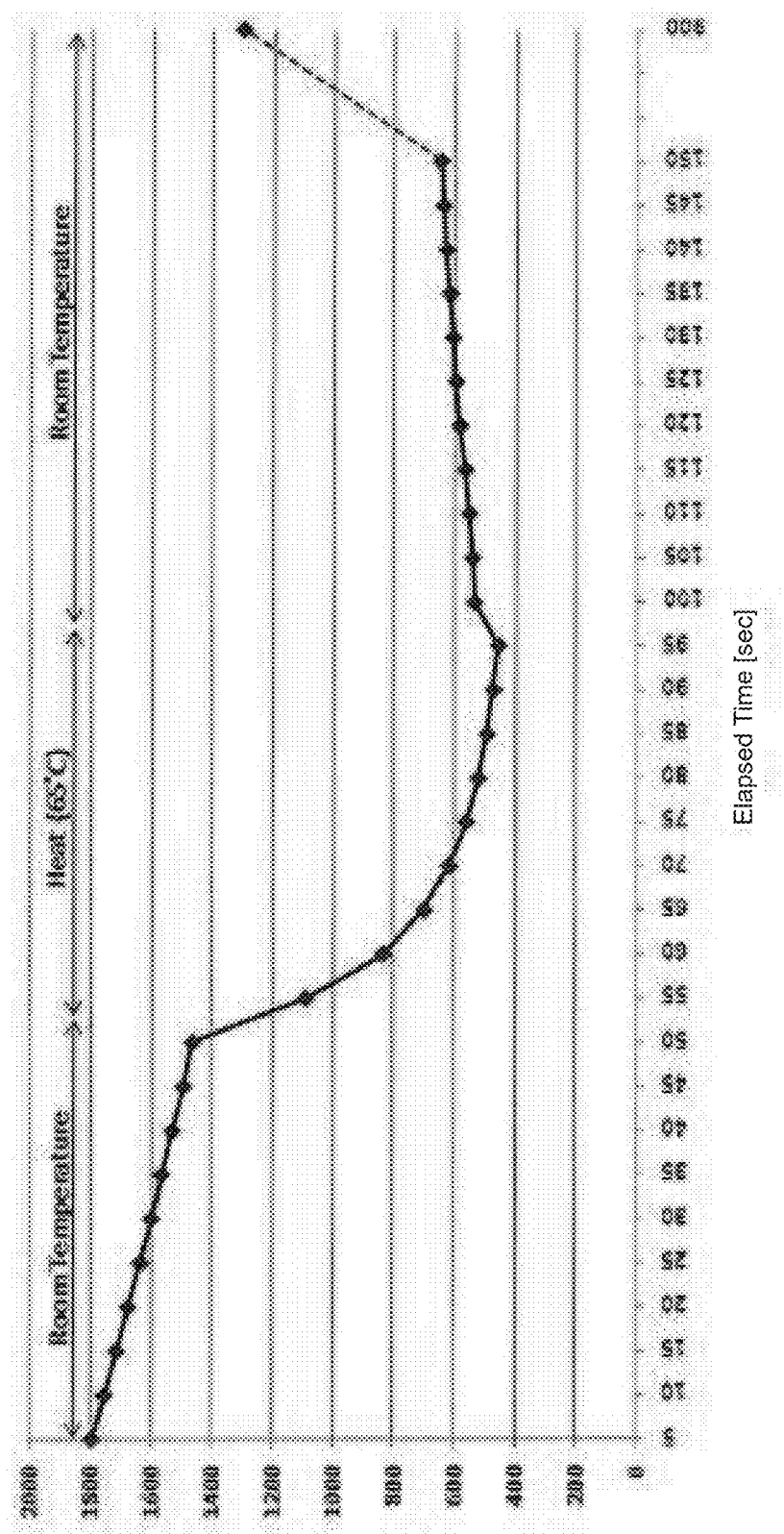
FIG. 28 A graph substituting a drawing and showing a change in a fluorescence intensity when a temperature is changed after copper sputtered on a glass surface is contacted with ssDNAs (Example 3).

After a predetermined time was elapsed from the contact of the nucleic acids with copper, a change in the fluorescence intensity by temperature change was examined. Immediately after the image has been captured, it held at room temperature. After 50 seconds, a heat block heated to 65° C. was gently placed over the Cu sputtered glass. After 100 seconds, the heat block was removed. The image was captured every 5 seconds. After 150 seconds, the measurement was stopped for now and the shutter for excitation light was closed. After 900 seconds, the measurement was again made. The results are shown in FIG. 28.

As shown in the Figure, the fluorescence intensity was gradually decreased for the first 50 seconds. This might be caused by fluorescence photobleaching. During the next 50 seconds, the fluorescence was disappeared at a speed apparently different from the fluorescence photobleaching. After the heat block was removed and it returned to room temperature, the fluorescence was gradually recovered. After 900 seconds, the fluorescence intensity was returned to a level that color degraded fluorescence intensity was subtracted from initial fluorescence intensity. These results show that the fluorescence emitted from the nucleic acids contacted with copper was heat sensitive, and was reversibly disappeared as the temperature increased.

Example 4

Example 4 illustrates that the cell nuclei could be fluorescently observed by introducing the sample containing cells onto the copper-sputtered glass.

<Material and Method>

As PBS, Dulbecco's Phosphate Buffered Saline, Ca/Mg free (Invitrogen Corporation, CA, USA) was used.

In an onion thin skin experiment, a commercially available onion thin skin was carefully peeled by a pair of tweezers, soaked into distilled water, rinsed and used. The onion thin skin was placed on the Cu sputtered glass, was soaked into the PBS, was covered by a cover glass, and was then observed.

In the experiment of a human leukocyte sample, IMMUNO-TROL Cells (Cat. No. 6607077, Beckman Coulter, Inc., Fullerton, Calif., USA) were treated as follows: Firstly, 500 microliters of the IMMUNO-TROL Cells were separated, cleaned with PBS, and settled using a centrifugal machine (1200 rpm, 5 min). Thereafter, a supernatant was discarded to flake pellets, water hemolysis treatments are repeated two times to provide a sample. The sample was diluted with PBS, thereby preparing a leukocyte sample. The water hemolysis treatment was performed as follows: After the pellets obtained as the result of the centrifugation were sufficiently flaked, 9 ml of deionized water was added, was mixed upside down for 30 seconds, 1 mL of 10×PBS Buffer (Nippon Gene Co., Ltd., Tokyo, Japan) was added and fully agitated. The cells were centrifuged (1200 rpm, 5 min) and were settled to remove a supernatant. The leukocyte sample was placed on the Cu sputtered glass, was covered by a cover glass, and was then observed.

The copper sputtered glass, the cover glass, the microscope etc. were the same as in Example 3. In the sputtering, a thickness was set to 20, 40, or 100 nm. The thickness was set to 40 nm in the following experiments, unless otherwise noted. When Cu was sputtered only on a part of a slide glass surface, a polyimide tape was adhered on the slide glass surface excluding a 5 mm square in a center part, thereby performing the sputtering. Then, the polyimide tape was removed. Thus, the Cu sputtered glass having a Cu layer only formed on the 5 mm square in the center part was produced.

The onion thin skin was fluorescently observed using an excitation filter: 365/10 nm, a dichroic mirror: 400 nm, and a fluorescent filter: 590LP. The leukocyte sample and Jurkat cells were fluorescently observed using a filter set UV-1A (Ex: 365/10, DM: 400, BA: 400/Nikon).

<Results>

Figure 29:
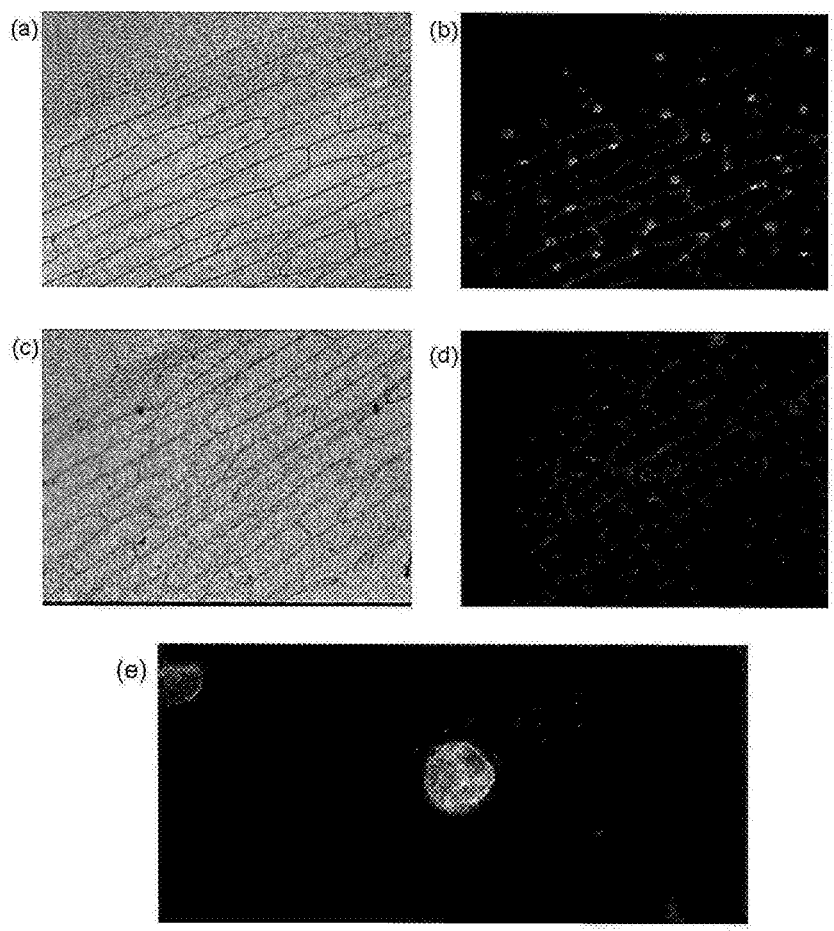
FIG. 29 Photographs each substituting a drawing and showing results of fluorescence observation of an onion thin skin on a copper sputtered glass (Example 4).

FIG. 29 shows images of the onion thin skin on the copper sputtered glass fluorescently observed and captured. (a) and (b) show observed images on the Cu sputtered glass. (c) and (d) show observed images on a slide glass without sputtering Cu thereon. (a) and (c) are bright field observed images. (b) and (d) are fluorescent images. (a) to (d) are images captured using a 10× objective lens. (e) is an image captured using a ×40 objective lens.

As shown in the Figures, strong fluorescence specific to the cell nuclei was observed on the cells over the Cu sputtered glass. Although slight fluorescence was observed on a part of cell walls and the like, it is considered as autofluorescence of the cell walls and the like, because it was observed on the cells over the slide glass without sputtering Cu thereon.

Figure 30:
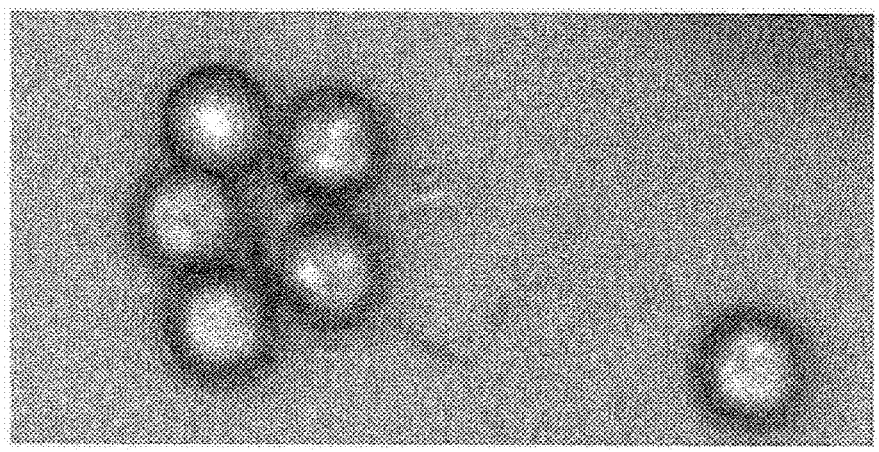
FIG. 30 Photographs each substituting a drawing and showing results of fluorescence observation of a human leukocyte sample on a copper sputtered glass (Example 4).
Figure 30:
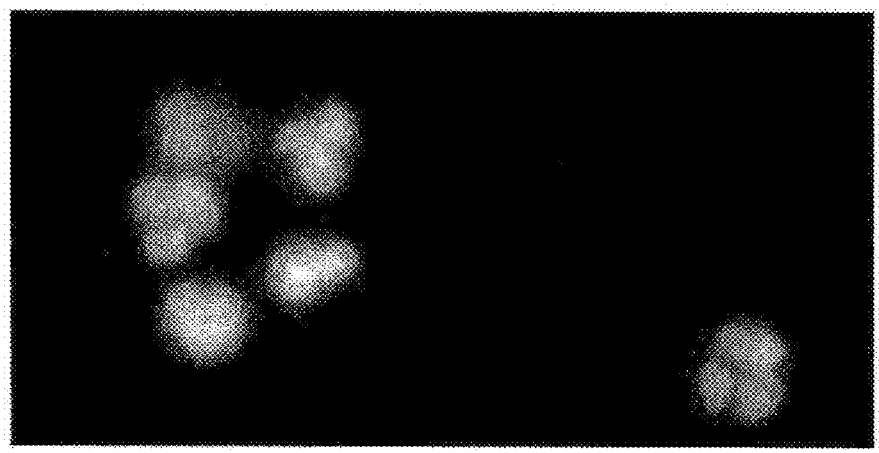

Next, animal cells were observed. FIG. 30 shows images acquired by fluorescently observing and capturing the human leukocyte sample on the copper sputtered glass. (a) is a bright field observed image. (b) is a fluorescent image. The ×40 objective lens was used.

In the fluorescent image, segmented neutrophils specific to the leukocyte were apparently observed.

Figure 31:
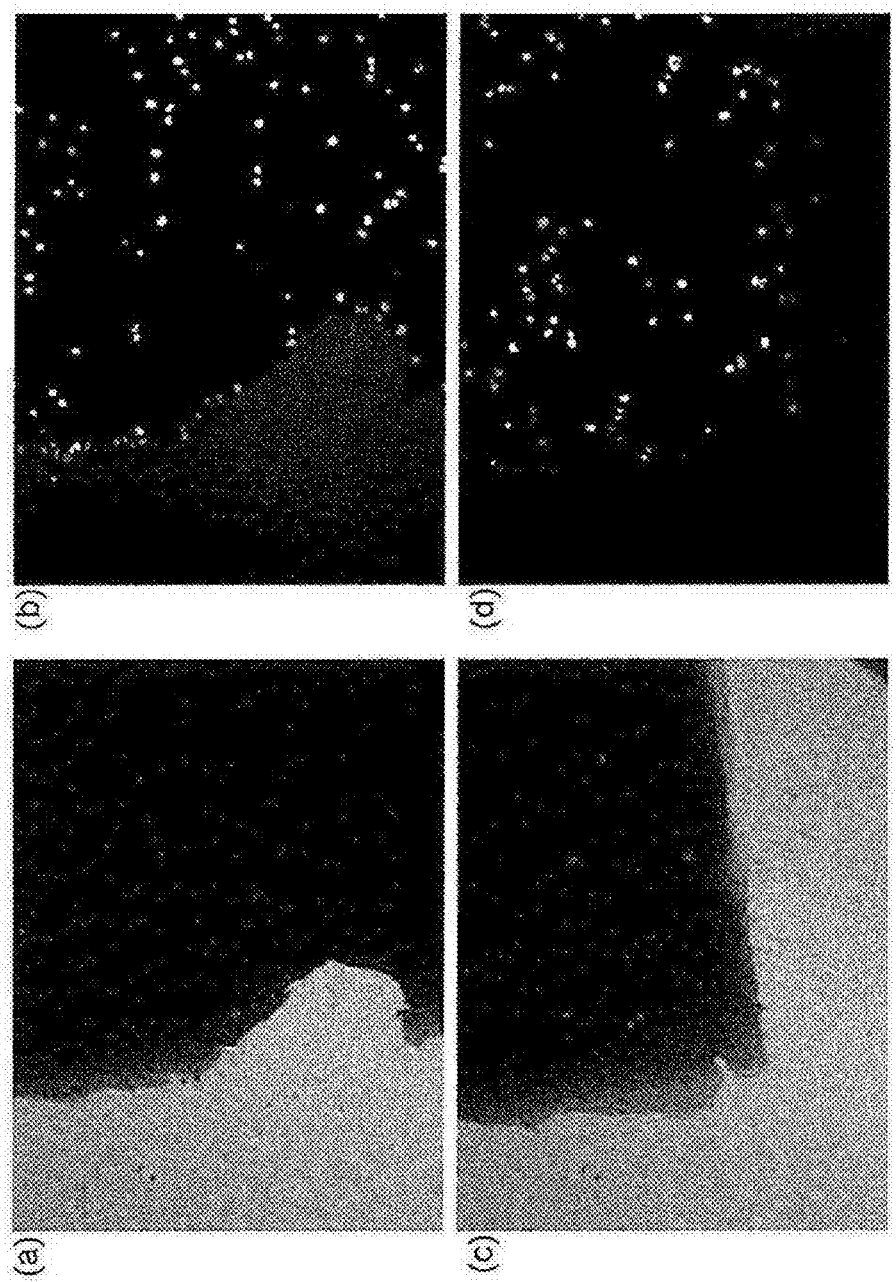
FIG. 31 Photographs each substituting a drawing and showing results of fluorescence observation of Jurkat cells on a copper sputtered glass (Example 4).

FIG. 31 shows images observed by using the Cu sputtered glass where Cu was sputtered only on a part of a slide glass surface. On the Cu sputtered glass, human leukocyte cell strains, i.e., Jurkat cells, were spread, were covered by the cover glass, and were then observed using the ×20 objective lens. The images were captured at a boundary between a Cu deposited area and a no Cu deposited area on the Cu sputtered glass. (a) and (c) are bright field observed images; black areas occupying more than half are areas where light is not permeated, because the Cu layers are formed. (b) and (d) are fluorescent images.

Figure 32:
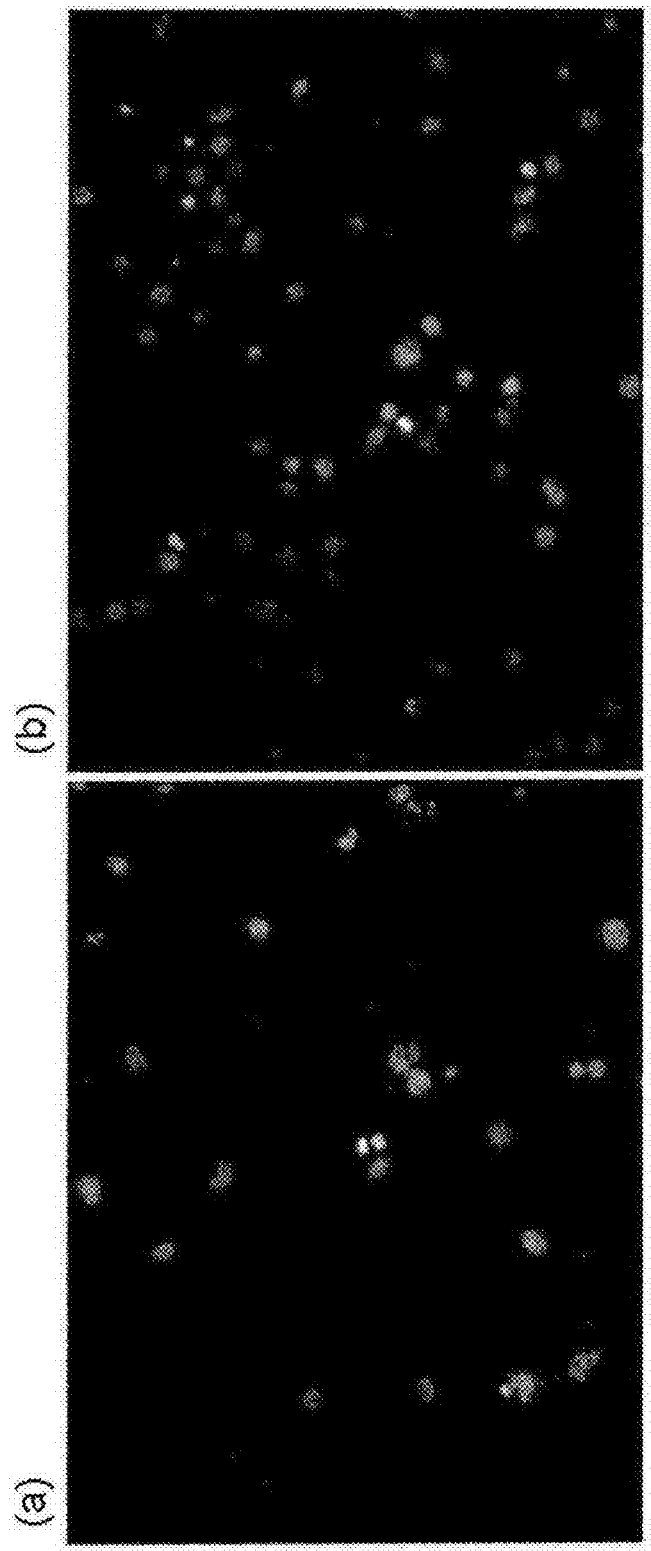
FIG. 32 Photographs each substituting a drawing and showing results of fluorescence observation of Jurkat cells on a copper sputtered glass (Example 4).

Strong fluorescence was observed only on the cell nuclei of the cells in the Cu deposited area. FIG. 32 shows observation results of the Jurkat cells using the Cu sputtered glass on which the Cu layer was formed in a thickness of 20 nm (a) or 100 nm (b). The fluorescence from the cell nuclei was observed at either thickness.

<Discussion>

The results in this Example show that the fluorescence can also be detected by bringing the cell nuclei into contact with copper. It is clear that the phenomenon occurs only on the glass substrate on which copper is sputtered, and is the result of the action between the cell nuclei and copper.

As a result of the fluorescence observation of the onion thin skin cells and the leukocyte cells, a difference between the shapes of cell nuclei in the cells was apparently shown. From this, according to the method of detecting nucleic acids of the present technology, different shapes of cell nuclei depending on the types of the cells can be identified.

Although not shown in this Example, in the experiment using the slide glass having copper sputtered on a part thereof, after the fluorescence was observed from only the cells on the Cu deposited area, the slide glass was inclined to move the cells from the Cu deposited area to the no Cu deposited area. After moving, the fluorescence was continuously observed. From this, even if the site where copper is contacted with the cells is spaced from the site where the cells are fluorescently observed, it is found that the fluorescence can be detected by disposing a means for moving the sample between the both sites.

After the fluorescence from the cell nuclei of the cells between the Cu sputtered glass and the cover glass was confirmed, the cover glass was removed and the solution containing the cells were exposed to air. Then, the fluorescence was quickly disappeared. Also in the experiment using Cu(II) ions and S.A. in Example 1, it was found that the fluorescence was disappeared after the reaction solution was exposed to air for a long time. The disappearance of the fluorescence could be considered due to oxidation of Cu(I) ions by the contact with air. Accordingly, the fluorescence generation may be inhibited by bringing the sample solution into contact with air (in particular, exposing to oxygen contained in the air). It is considered that the method of detecting nucleic acids according to the present technology is preferably performed by limiting the contact with air, e.g., in the microchip.

Example 5

In Example 5, the cell nucleus observation substrate according to the present invention was used, and cells labeled with magnetic labeled antibodies were selected and concentrated to observe the nuclear fluorescence staining image.

<Material and Method>

Substrate: Micro Slide Glass (Matsunami, Japan) and Gap cover glass (Matsunami, Japan) were pressed. As an absorption member, BEMCOT, M-3 (Asahi Kasei Corp., Japan) was inserted into the Gap cover glass at one end. In the experiment using a copper sputtering, Cu was sputtered on a surface of the Micro Slide Glass at 40 nm.

Magnetic labeled antibody: MACS CD45 MicroBeads (hereinafter referred to as "MACS-CD45") was obtained from Miltenyi Biotech GmbH (Germany). EasySep Human CD45 Depletion Cocktail (hereinafter referred to as "EasySep-CD45") was obtained from StemCell Technologies, Inc. (Canada). EasySep-CD45 has stronger magnetism than MACS-CD45.

Cell: Jurkat cells were used. A sample of the cells was adjusted to be $1.75 \times 10^7$ cells/mL. To 200 µl of the sample, 5 µl EasySep-CD45 or 10 µl of MACS-CD45 were added, which was incubated for 15 minutes. To the EasySep-CD45 sample, 10 µl of an EasySep magnet reagent was further added, which was incubated for 10 minutes. In the experiment using a copper sputtering, the cells were washed twice with PBS after incubation.

Magnetic adsorption of cells: The magnet used was a neodymium magnet having a cylindrical shape with a diameter of 5 mm and a height of 3 mm. The magnet was disposed in contact with an upper surface of the Gap cover glass. The cells labeled with the magnetic substance flowed into a gap having a depth of 20 micrometers formed between a lower surface of the Gap cover glass and the slide glass, whereby the cells labeled with the magnetic substance were accumulated around the magnet disposed.

Figure 33:
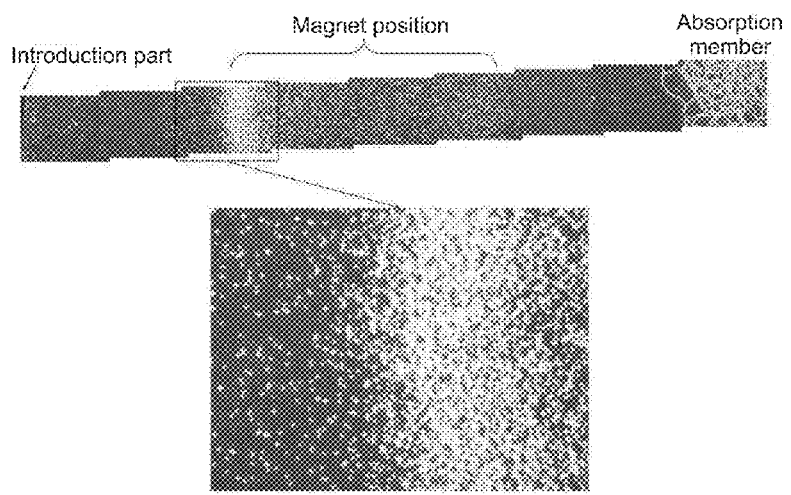
FIG. 33 Photographs each substituting a drawing and showing magnetic labeled antibodies (EasySep-CD45) labeled cells accumulated on the observation area of the substrate by a magnet in Example 5.
Figure 34:
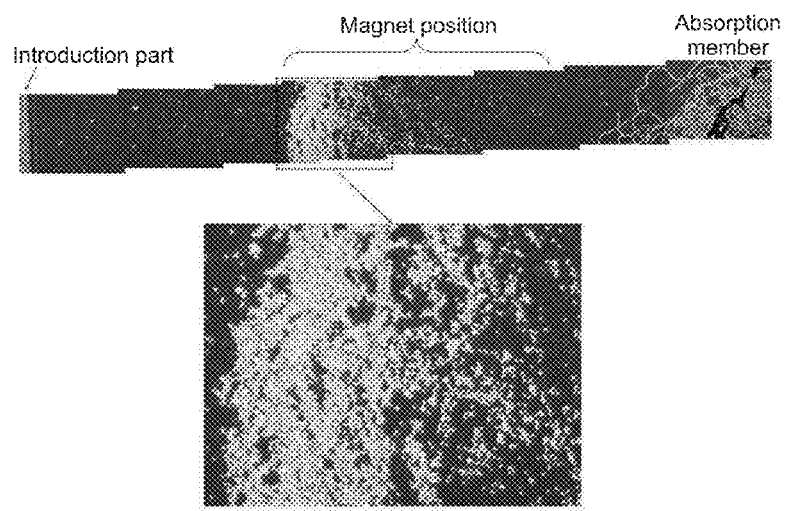
FIG. 34 Photographs each substituting a drawing and showing magnetic labeled antibodies (MACS-CD45) labeled cells accumulated on the observation area of the substrate by a magnet in Example 5.

FIG. 33 shows photographs of EasySep-CD45 labeled cells accumulated on the observation area of the substrate, and FIG. 34 shows photographs of MACS-CD45 labeled cells. In the Figures, at left hand, the introduction part into which the sample liquid is introduced is positioned. At right hand, the absorption member for absorbing the sample is positioned. At center, the observation area to which the magnet is disposed is positioned. The photographs were taken after the magnet was removed. It was confirmed that the EasySep-CD45 labeled cells and the MACS-CD45 labeled cells were accumulated on the observation area corresponding to the position at which the magnet was disposed. The lower photographs were magnified photographs of a part (an introduction part side) of the observation area.

Figure 35:
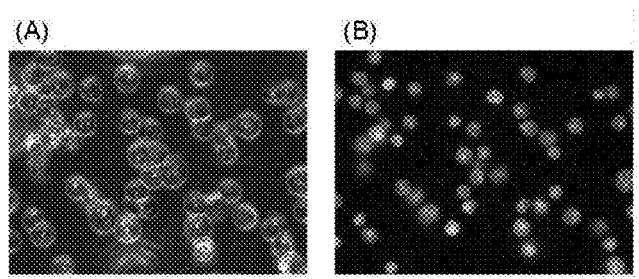
FIG. 35 Photographs each substituting a drawing and showing a permeated image (A) and a fluorescence image (B) captured of magnetic labeled antibodies (MACS-CD45) labeled cells accumulated on the observation area of the substrate on which copper was sputtered in Example 5.

FIG. 35 shows a permeated image (A) captured of the MACS-CD45 labeled cells accumulated on the observation area of the substrate on which copper was sputtered, and a fluorescence image (B) acquired by irradiating the ultraviolet rays. In the fluorescence image (B), the cell nuclei accumulated show fluorescence, and nucleic shapes are obviously observed.

INDUSTRIAL APPLICABILITY

By the cell nucleus observation substrate according to the present invention, nuclei of cells, microorganisms and the like can be stained by a simple operation and observed their forms. Accordingly, the cell nucleus observation substrate according to the present invention can be effectively used for determination of types or properties of cells, microorganisms, and the like based on forms of cell nuclei in a variety of fields including a medical field, a drug discovery field, a food field, an agricultural field and the like.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

DESCRIPTION OF SYMBOLS

A cell nucleus observation apparatus
1 introduction part
2 observation area
3 copper film
4 absorption member
5 magnet
6 outlet
$a_1$, $a_2$ substrate layer
$a_3$ spacer

The invention claimed is:

1. A cell nucleus observation substrate, comprising:
a pair of first and second substrate layers extending at a predetermined distance, defining a space therebetween;
an introduction part disposed within the space, into which a sample liquid containing a cell is introduced;
an absorption member disposed at one end of the space, opposite to the introduction part, such that the absorption member absorbs the introduced sample liquid;
an observation area disposed within the space, within which the cell in the sample liquid introduced from the introduction part is held; and
a copper film coupled to the second substrate layer within the introduction part and the observation area for contacting the sample liquid.

2. The cell nucleus observation substrate according to claim 1, wherein the sample liquid defines a flow path, and the copper film extends along at least a part of the flow path.

3. The cell nucleus observation substrate according to claim 2, comprising a magnet detachably coupled to the first substrate layer and forming a magnetic field within the observation area, wherein the cell in the sample liquid flowing through the flow path is held within the observation area based on a magnetic force.

4. The cell nucleus observation substrate according to claim 3, wherein the magnet is attached at a position between the introduction part and the absorption member.

5. A cell nucleus observation apparatus, comprising:
a pair of first and second substrate layers extending at a predetermined distance, defining a space therebetween;
an introduction part disposed within the space, into which a sample liquid containing a cell is introduced;
an absorption member disposed at one end of the space, opposite to the introduction part, such that the absorption member absorbs the introduced sample liquid;
an observation area disposed within the space, within which the cell in the sample liquid introduced from the introduction part is held;
a copper film coupled to the second substrate layer within the introduction part and the observation area for contacting with the sample liquid; and
an optical detecting means for irradiating a light to the observation area and detecting fluorescence generated.

6. The cell nucleus observation substrate according to claim 5, wherein a wavelength of the light irradiated by the optical detecting means is 300 to 420 nm.

7. The cell nucleus observation substrate according to claim 1, wherein thickness of the space is 10 to 50 micrometers.

* * * * *

```
                        SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: oligo-DNA

<400> SEQUENCE: 1
aaaaaaaaaa aaaaaaaaaa                                                    20

<210> SEQ ID NO 2
<211> LENGTH: 20
<212> TYPE: DNA
<213> ORGANISM: Artificial Sequence
<220> FEATURE:
<223> OTHER INFORMATION: oligo-DNA

<400> SEQUENCE: 2
tttttttttt tttttttttt                                                    20

<210> SEQ ID NO 3
<211> LENGTH: 20
<212> TYPE: DNA
<213> ORGANISM: Artificial Sequence
<220> FEATURE:
<223> OTHER INFORMATION: oligo-DNA

<400> SEQUENCE: 3
gggggggggg gggggggggg                                                    20

<210> SEQ ID NO 4
<211> LENGTH: 20
<212> TYPE: DNA
<213> ORGANISM: Artificial Sequence
<220> FEATURE:
<223> OTHER INFORMATION: oligo-DNA

<400> SEQUENCE: 4
cccccccccc cccccccccc                                                    20

<210> SEQ ID NO 5
```

```
<211> LENGTH: 20
<212> TYPE: DNA
<213> ORGANISM: Artificial Sequence
<220> FEATURE:
<223> OTHER INFORMATION: oligo-DNA

<400> SEQUENCE: 5
aaaaaataaa taataaaaaa                                              20

<210> SEQ ID NO 6
<211> LENGTH: 20
<212> TYPE: DNA
<213> ORGANISM: Artificial Sequence
<220> FEATURE:
<223> OTHER INFORMATION: oligo-DNA

<400> SEQUENCE: 6 tttttatta tttattttt                                                20

<210> SEQ ID NO 7
<211> LENGTH: 20
<212> TYPE: DNA
<213> ORGANISM: Artificial Sequence
<220> FEATURE:
<223> OTHER INFORMATION: oligo-DNA

<400> SEQUENCE: 7
ggggggcggg cggcggggggg                                             20

<210> SEQ ID NO 8
<211> LENGTH: 20
<212> TYPE: DNA
<213> ORGANISM: Artificial Sequence
<220> FEATURE:
<223> OTHER INFORMATION: oligo-DNA

<400> SEQUENCE: 8
ccccccgccg cccgccccccc                                             20

<210> SEQ ID NO 9
<211> LENGTH: 20
<212> TYPE: DNA
<213> ORGANISM: Artificial Sequence
<220> FEATURE:
<223> OTHER INFORMATION: oligo-DNA

<400> SEQUENCE: 9 aaaattttt tttttaaaa                                                20

<210> SEQ ID NO 10
<211> LENGTH: 6
<212> TYPE: DNA
<213> ORGANISM: Artificial Sequence
<220> FEATURE:
<223> OTHER INFORMATION: oligo-DNA

<400> SEQUENCE: 10 tttttt                                                              6

<210> SEQ ID NO 11
<211> LENGTH: 3
<212> TYPE: DNA
<213> ORGANISM: Artificial Sequence
<220> FEATURE:
<223> OTHER INFORMATION: oligo-DNA

<400> SEQUENCE: 11
```

-continued aaa                                                                     3

<210> SEQ ID NO 12
<211> LENGTH: 3
<212> TYPE: DNA
<213> ORGANISM: Artificial Sequence
<220> FEATURE:
<223> OTHER INFORMATION: oligo-DNA

<400> SEQUENCE: 12 ttt                                                                     3

<210> SEQ ID NO 13
<211> LENGTH: 3
<212> TYPE: DNA
<213> ORGANISM: Artificial Sequence
<220> FEATURE:
<223> OTHER INFORMATION: oligo-DNA

<400> SEQUENCE: 13 tta                                                                     3

<210> SEQ ID NO 14
<211> LENGTH: 3
<212> TYPE: DNA
<213> ORGANISM: Artificial Sequence
<220> FEATURE:
<223> OTHER INFORMATION: oligo-DNA

<400> SEQUENCE: 14 tat                                                                     3

<210> SEQ ID NO 15
<211> LENGTH: 3
<212> TYPE: DNA
<213> ORGANISM: Artificial Sequence
<220> FEATURE:
<223> OTHER INFORMATION: oligo-DNA

<400> SEQUENCE: 15 att                                                                     3

<210> SEQ ID NO 16
<211> LENGTH: 3
<212> TYPE: DNA
<213> ORGANISM: Artificial Sequence
<220> FEATURE:
<223> OTHER INFORMATION: oligo-DNA

<400> SEQUENCE: 16 taa                                                                     3

<210> SEQ ID NO 17
<211> LENGTH: 3
<212> TYPE: DNA
<213> ORGANISM: Artificial Sequence
<220> FEATURE:
<223> OTHER INFORMATION: oligo-DNA

<400> SEQUENCE: 17 ata                                                                     3

<210> SEQ ID NO 18
<211> LENGTH: 3
<212> TYPE: DNA

```
<213> ORGANISM: Artificial Sequence
<220> FEATURE:
<223> OTHER INFORMATION: oligo-DNA

<400> SEQUENCE: 18 aat                                                                      3

<210> SEQ ID NO 19
<211> LENGTH: 10
<212> TYPE: DNA
<213> ORGANISM: Artificial Sequence
<220> FEATURE:
<223> OTHER INFORMATION: oligo-DNA

<400> SEQUENCE: 19
tttttttttt                                                              10

<210> SEQ ID NO 20
<211> LENGTH: 10
<212> TYPE: DNA
<213> ORGANISM: Artificial Sequence
<220> FEATURE:
<223> OTHER INFORMATION: oligo-DNA

<400> SEQUENCE: 20
uuuuuuuuug                                                              10

<210> SEQ ID NO 21
<211> LENGTH: 20
<212> TYPE: DNA
<213> ORGANISM: Artificial Sequence
<220> FEATURE:
<223> OTHER INFORMATION: oligo-DNA

<400> SEQUENCE: 21
cccctttttt tttttttcccc                                                  20

<210> SEQ ID NO 22
<211> LENGTH: 20
<212> TYPE: DNA
<213> ORGANISM: Artificial Sequence
<220> FEATURE:
<223> OTHER INFORMATION: oligo-DNA

<400> SEQUENCE: 22
ccccccccct tttttttttt                                                   20

<210> SEQ ID NO 23
<211> LENGTH: 20
<212> TYPE: DNA
<213> ORGANISM: Artificial Sequence
<220> FEATURE:
<223> OTHER INFORMATION: oligo-DNA

<400> SEQUENCE: 23
tttttttttt ttcccccccc                                                   20

<210> SEQ ID NO 24
<211> LENGTH: 20
<212> TYPE: DNA
<213> ORGANISM: Artificial Sequence
<220> FEATURE:
<223> OTHER INFORMATION: oligo-DNA

<400> SEQUENCE: 24
ccttttttcc ccttttttcc                                                   20
```

```
<210> SEQ ID NO 25
<211> LENGTH: 20
<212> TYPE: DNA
<213> ORGANISM: Artificial Sequence
<220> FEATURE:
<223> OTHER INFORMATION: oligo-DNA

<400> SEQUENCE: 25
ctttcctttc ctttcctttc                                                    20

<210> SEQ ID NO 26
<211> LENGTH: 20
<212> TYPE: DNA
<213> ORGANISM: Artificial Sequence
<220> FEATURE:
<223> OTHER INFORMATION: oligo-DNA

<400> SEQUENCE: 26
ccttcttctt cttcttcttc                                                    20
```